United States Patent
Kalidas et al.

(10) Patent No.: US 12,268,527 B2
(45) Date of Patent: Apr. 8, 2025

(54) SYSTEM AND METHOD FOR AUTOMATED ANALYSIS AND DETECTION OF CARDIAC ARRHYTHMIAS FROM ELECTROCARDIOGRAMS

(71) Applicant: Board of Regents, The University of Texas System, Austin, TX (US)

(72) Inventors: Vignesh Kalidas, Richardson, TX (US); Lakshman S. Tamil, Plano, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 725 days.

(21) Appl. No.: 17/380,765

(22) Filed: Jul. 20, 2021

(65) Prior Publication Data

US 2022/0015711 A1   Jan. 20, 2022

Related U.S. Application Data

(60) Provisional application No. 63/054,166, filed on Jul. 20, 2020.

(51) Int. Cl.
*A61B 5/00* (2006.01)
*A61B 5/352* (2021.01)
(Continued)

(52) U.S. Cl.
CPC .......... *A61B 5/7203* (2013.01); *A61B 5/0006* (2013.01); *A61B 5/0022* (2013.01);
(Continued)

(58) Field of Classification Search
CPC ... A61B 5/7203; A61B 5/0006; A61B 5/0022; A61B 5/352; A61B 5/361; A61B 5/364;
(Continued)

(56) References Cited

U.S. PATENT DOCUMENTS

| | | | | |
|---|---|---|---|---|
| 2009/0299204 | A1* | 12/2009 | Hsieh | A61B 5/318 600/509 |
| 2010/0099995 | A1* | 4/2010 | Lian | A61N 1/3702 600/509 |

(Continued)

OTHER PUBLICATIONS

World Congress on Medical Physics and Biomedical Engineering Sep. 7-12, 2009 Munich, Germany: vol. 25/VII Diagnostic and Therapeutic Instrumentation, Clinical Engineering. Germany, Springer Berlin Heidelberg, 2010. (Year: 2009).*

(Continued)

*Primary Examiner* — James M Kish
*Assistant Examiner* — Paroma Mukhopadhyay
(74) *Attorney, Agent, or Firm* — Thomas Horstemeyer, LLP

(57) ABSTRACT

The present disclosure presents arrhythmia analysis systems and methods. One such method comprises processing an acquired ECG waveform signal to remove noise artifacts and form a denoised ECG waveform signal; processing the denoised ECG waveform signal to remove low quality segments and form a high quality ECG waveform signal; analyzing the high quality ECG waveform to detect a presence of a beat-independent ventricular arrhythmia; processing the denoised ECG signal to extract beat (R-peak) locations corresponding to QRS complexes from the denoised ECG signal; analyzing the denoised ECG signal to detect a presence of a beat-dependent ventricular arrhythmia based on the extracted beat (R-peak) locations; analyzing the denoised ECG signal to detect a presence of one or more supraventricular arrhythmias based on the extracted beat locations of the ECG signal; and outputting a report containing one or more arrhythmias detected by the analyzing steps. Other methods/systems are also provided.

21 Claims, 25 Drawing Sheets

(51) Int. Cl.
- A61B 5/361 (2021.01)
- A61B 5/364 (2021.01)
- G06N 3/045 (2023.01)
- G06N 3/088 (2023.01)
- G06N 20/20 (2019.01)
- G16H 15/00 (2018.01)
- G16H 50/30 (2018.01)

(52) U.S. Cl.
CPC .............. *A61B 5/352* (2021.01); *A61B 5/361* (2021.01); *A61B 5/364* (2021.01); *G06N 3/045* (2023.01); *G06N 3/088* (2013.01); *G06N 20/20* (2019.01); *G16H 15/00* (2018.01); *G16H 50/30* (2018.01)

(58) Field of Classification Search
CPC ........ G06N 3/045; G06N 3/088; G06N 20/20; G16H 15/00; G16H 50/30
USPC ....... 600/508, 509, 515, 516, 517, 518, 521, 600/523
See application file for complete search history.

(56) References Cited

U.S. PATENT DOCUMENTS

| | | | | |
|---|---|---|---|---|
| 2020/0054292 | A1* | 2/2020 | Govari | G16H 50/20 |
| 2020/0138306 | A1* | 5/2020 | Li | A61B 5/7267 |
| 2021/0100471 | A1* | 4/2021 | Yu | G16H 50/20 |
| 2021/0345934 | A1* | 11/2021 | Landgraf | A61B 5/0022 |
| 2021/0369131 | A1* | 12/2021 | Cao | A61B 5/02455 |
| 2021/0401534 | A1* | 12/2021 | Grass | A61B 90/37 |

OTHER PUBLICATIONS

Chui RW, Derakhchan K, Vargas HM. Comprehensive analysis of cardiac arrhythmias in telemetered cynomolgus monkeys over a 6-month period. J Pharmacol Toxicol Methods. Sep. 2012;66(2):84-91. doi: 10.1016/j.vascn.2012.05.002. Epub May 14, 2012. PMID: 22613062. (Year: 2012).*

Hannun AY, et al. Cardiologist-level arrhythmia detection and classification in ambulatory electrocardiograms using a deep neural network. Nat Med. Jan. 2019;25(1):65-69. doi: 10.1038/s41591-018-0268-3. Epub Jan. 7, 2019. Erratum in: Nat Med. 2019 (Year: 2019).*

Fung et al. Electrocardiographic patch devices and contemporary wireless cardiac monitoring. Front Physiol. May 27, 2015;6:149. doi: 10.3389/fphys.2015.00149. PMID: 26074823; PMCID: PMC4444741. (Year: 2015).*

Kandola, Everything you need to know about trigeminy, May 7, 2020, Medical News Today (Year: 2020).*

Verma, Anurag, and Xiaodai Dong. "Detection of ventricular fibrillation using random forest classifier." Journal of Biomedical Science and Engineering 9.5 (2016): 259-268. (Year: 2016).*

Xiong, Peng, et al. "ECG signal enhancement based on improved denoising auto-encoder." Engineering Applications of Artificial Intelligence 52 (2016): 194-202. (Year: 2016).*

Gordon, Max, and Cranos Williams. "PVC detection using a convolutional autoencoder and random forest classifier." Biocomputing 2019: Proceedings of the Pacific Symposium. 2018. (Year: 2019).*

Gertsch, Marc. The ECG Manual: An Evidence-Based Approach. Netherlands, Springer London, 2008. (Year: 2008).*

* cited by examiner

```
                              ECG ANALYSIS REPORT
Filename : tri.csv
Source   : Web Upload ECG Analysis Summary
--------------------

This ECG shows signs of ventricular bigeminy and ventricular trigeminy.

Analysis Results
----------------

Processing time (hh:mm:ss)           : 00:00:10

ECG duration (hh:mm:ss)              : 00:00:30

Noisy segments                       : 0 (0 hours, 0 minutes and 0 seconds)

Number of beats                      : 33
Average heart rate                   : 66.37 bpm Number of probable PVCs              : 11
Number of probable PACs              : 0

Sustained VT/VF episodes             : 0 (0 hours, 0 minutes and 0 seconds)

Short VT episodes                    : 0 (0 hours, 0 minutes and 0 seconds)

Ventricular couplet episodes         : 0 (0 hours, 0 minutes and 0 seconds)

Ventricular bigeminy episodes        : 1 (0 hours, 0 minutes and 6 seconds)
      >> Episode 1    : 00:00:03 to 00:00:10

Ventricular trigeminy episodes       : 1 (0 hours, 0 minutes and 12 seconds)
      >> Episode 1    : 00:00:10 to 00:00:23

Ventricular quadrigeminy episodes    : 0 (0 hours, 0 minutes and 0 seconds)

Other ventricular episodes           : 0 (0 hours, 0 minutes and 0 seconds)

Atrial fibrillation episodes         : 0 (0 hours, 0 minutes and 0 seconds)

Sinus bradycardia episodes           : 0 (0 hours, 0 minutes and 0 seconds)

Supraventricular tachycardia episodes: 0 (0 hours, 0 minutes and 0 seconds)

Supraventricular couplet episodes    : 0 (0 hours, 0 minutes and 0 seconds)

Supraventricular bigeminy episodes   : 0 (0 hours, 0 minutes and 0 seconds)

Supraventricular trigeminy episodes  : 0 (0 hours, 0 minutes and 0 seconds)

Supraventricular quadrigeminy episodes: 0 (0 hours, 0 minutes and 0 seconds)
```

FIG. 3B

| Validation Dataset Confusion Matrix | | | |
|---|---|---|---|
|  | noisy | clean |  |
| NOISY | 5128 (TP) | 20 (FN) | 5148 |
| CLEAN | 21 (FP) | 4731 (TN) | 4752 |
|  | 5149 | 4751 | 9900 |

FIG. 5

| Training dataset confusion matrix | | | |
|---|---|---|---|
|  | vt/vf | non vt/vf |  |
| VT/VF | 3088 (TP) | 36 (FN) | 3124 |
| NON VT/VF | 123 (FP) | 7835 (TN) | 7958 |
|  | 3211 | 7871 | 11082 |

FIG. 13

| Validation dataset confusion matrix | | | |
|---|---|---|---|
|  | vt/vf | non vt/vf |  |
| VT/VF | 2377 (TP) | 51 (FN) | 2428 |
| NON VT/VF | 105 (FP) | 8619 (TN) | 8724 |
|  | 2482 | 8670 | 11152 |

FIG. 14

| Training dataset (MITDB – DS1) confusion matrix | | | |
|---|---|---|---|
| | pvc | non pvc | |
| PVC | 3680 (TP) | 0 (FN) | 3680 |
| NON PVC | 54 (FP) | 47001 (TN) | 47055 |
| | 3734 | 47001 | 50735 |

FIG. 17

| Validation dataset (MITDB – DS2) confusion matrix | | | |
|---|---|---|---|
| | pvc | non pvc | |
| PVC | 2982 (TP) | 236 (FN) | 3218 |
| NON PVC | 138 (FP) | 46232 (TN) | 46370 |
| | 3120 | 46468 | 49588 |

FIG. 18

| Test dataset (INCARTDB) confusion matrix | | | |
|---|---|---|---|
| | pvc | non pvc | |
| PVC | 17607 (TP) | 2383 (FN) | 19990 |
| NON PVC | 973 (FP) | 154711 (TN) | 155684 |
| | 18580 | 157094 | 175674 |

FIG. 19

Comparison with State-of-the-Art Methods for Records in the MITDB-S2 Dataset

| Method | Se | PPV | FSc |
|---|---|---|---|
| (Llamedo and Martínez, 2011) | 83.0% | 88.0% | 85.4% |
| (Llamedo and Martínez, 2012) | 89.0% | 87.0% | 88.0% |
| (de Chazal and Reilly, 2006)[a] | 94.3% | 94.3% | 94.3% |
| (Oster et al., 2015)[b] | 92.7% | 96.2% | 94.5% |
| (Kiranyaz et al., 2016)[c,d] | 93.9% | 90.6% | 92.2% |
| (Ortín et al., 2019)[d] | 95.4% | 88.8% | 92.0% |
| SSAE-RF classifier (this dissertation) | 92.7% | 95.6% | 94.1% |

[a] 500 beats per record were used for training
[b] Semi-supervised approach with expert assistance
[c] First five minutes per record were used for training
[d] Results are for entire MITDB database (MITDB-DS1 and MITDB-DS2)

FIG. 21

Comparison with State-of-the-Art Methods for Records in the INCARTDB Dataset

| Method | Se | PPV | F1 |
| --- | --- | --- | --- |
| (Llamedo and Martínez, 2011)[a,b] | 82.0% | 88.4% | 85.1% |
| (Llamedo and Martínez, 2012)[a,b] | 88.0% | 96.0% | 91.8% |
| (Oster et al., 2015)[b,c] | 95.4% | 99.3% | 97.3% |
| SSAE-RF classifier (this dissertation) | 88.1% | 94.8% | 91.3% |

[a]Fusion beats are considered as PVCs
[b]Multi-lead ECG information used (leads II and V1)
[c]Semi-supervised approach with expert assistance

FIG. 22

Comparison with Other State-of-the-Art Methods

| Method | Remarks | Database | Se | Sp |
|---|---|---|---|---|
| AF_model (this dissertation) | HRD[a] | AFDB | 96.8% | 99.2% |
| | | MITDB | 99.2% | 97.1% |
| (Moody, 1983) | HRD[a] | AFDB | 93.5% | N/A |
| | | MITDB | N/A | N/A |
| (Tateno and Glass, 2001) | HRD | AFDB | 94.4% | 97.2% |
| | | MITDB | 88.2% | 87.0% |
| (Dash et al., 2009) | HRD | AFDB | 94.4% | 95.1% |
| | | MITDB | 90.2% | 91.2% |
| (Asgari et al., 2015) | HRI[b] | AFDB | 97.0% | 97.1% |
| | | MITDB | N/A | N/A |
| (Ladavich and Ghoraani, 2015) | HRI | AFDB | 98.1% | 91.7% |
| | | MITDB | N/A | N/A |
| (Babaeizadeh et al., 2009) | HRD+AA[c] | AFDB | 93.0% | 98.0% |
| | | MITDB | N/A | N/A |
| (Xia et al., 2018) | HRD+AA | AFDB | 98.8% | 97.9% |
| | | MITDB | N/A | N/A |

[a] Heart Rate Dependent methods
[b] Heart Rate Independent methods
[c] AA indicates atrial activity analysis

FIG. 25

SYSTEM AND METHOD FOR AUTOMATED ANALYSIS AND DETECTION OF CARDIAC ARRHYTHMIAS FROM ELECTROCARDIOGRAMS

CROSS-REFERENCE TO RELATED APPLICATION

This application claims priority to U.S. provisional application entitled, "System and Method for Automated Analysis and Detection of Cardiac Arrhythmias from Electrocardiograms," having Ser. No. 63/054,166, filed Jul. 20, 2020, which is entirely incorporated herein by reference.

TECHNICAL FIELD

The present disclosure relates to a system and method for determining cardiac arrhythmias from electrocardiogram (ECG) waveforms.

BACKGROUND

Cardiac Arrhythmias are cardiac abnormalities that arise as a consequence of irregularities in the electrical conduction system of the heart. The Sino-Atrial (SA) node, also known as heart's natural pacemaker, initiates electrical impulses that traverse through the cardiac chambers in an ordered manner, resulting in completion of one cardiac cycle i.e., one heartbeat. Any deviation from a normal conduction sequence of these electrical impulses, in terms of conduction rate, regularity or excitation by sources other than the SA node, results in cardiac arrhythmias. Cardiac arrhythmias can be short term or persistent, symptomatic or asymptomatic, and benign or life-threatening, depending on the type and cause of dysrhythm. More than four million Americans are affected by some form of arrhythmia with increased prevalence among the elderly population. Prevalence of Premature Ventricular Complexes (PVCs) is about 69% in adults over 75 years while atrial Fibrillation is prevalent in about 2.7 million Americans and is expected to reach 12.1 million by 2030. These arrhythmias are highly correlated with congestive heart failure, stroke, high blood pressure and possible sleep apnea. Oftentimes, delayed diagnosis can increase severity of these arrhythmias and therefore, timely and accurate detection of arrhythmias is vital for patient care and well-being in the long term.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 3B is an example ECG analysis report in accordance with an embodiment of the present disclosure.

FIG. 5 shows a confusion matrix for electrode motion (EM) noise classification on a validation dataset in accordance with various embodiments of the present disclosure.

FIG. 13 shows a confusion matrix depicting model performance on a training dataset during an exemplary ventricular fibrillation analysis stage in accordance with various embodiments of the present disclosure.

FIG. 14 shows a confusion matrix depicting model performance on a validation dataset in accordance with various embodiments of the present disclosure.

FIGS. 17-19 shows a confusion matrix depicting model performance on training dataset, a validation dataset, and a test dataset, respectively, for exemplary arrhythmia analysis algorithm and related processes in detecting the occurrence of PVCs in accordance with various embodiments of the present disclosure.

FIG. 25 provides a table of performance statistics comparing an exemplary atrial fibrillation detection algorithm with other state-of-the-art methods.

DETAILED DESCRIPTION

Figure 1:
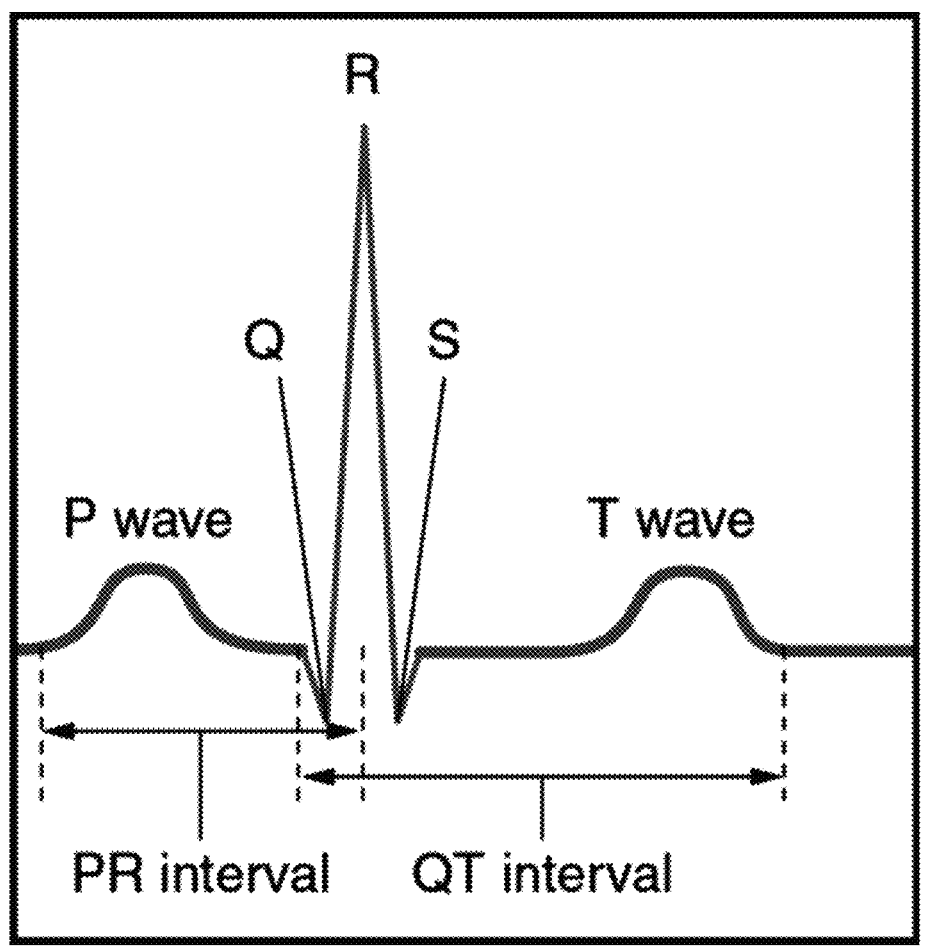
FIG. 1 shows the primary components of an electrocardiogram (ECG) signal.

Proper functioning of the cardiovascular system is essential for survival and conditions that result in abnormal functioning of the cardiovascular system can have serious short-term and long-term consequences on an individual's health and life. The present disclosure describes various systems and methods for detecting of a particular class of cardiac abnormalities, termed cardiac arrhythmias.

Cardiac arrhythmias that originate in the ventricles are termed ventricular arrhythmias whereas those that originate above the ventricles are termed supraventricular arrhythmias. The latter includes both atrial (originating in the atria) and junctional (originating in the AV junction) arrhythmias. A third category of arrhythmias is known as sinus arrhythmias and occurs as a consequence of irregularities in the SA node. Accordingly, in certain embodiments of the present disclosure, a comprehensive set of machine learning techniques, e.g., Deep Learning and Random Forests based and complemented by logical analysis techniques, are used to detect different cardiac arrhythmias (and include the three types of dysrhythms) in a fully automated manner. This includes, along with normal sinus rhythm, (1) ventricular fibrillation (VF) and Sustained Ventricular Tachycardia, (2) premature ventricular complexes (PVC), (3) ventricular bigeminy, (4) ventricular trigeminy, (5) ventricular quadrigeminy, (6) ventricular couplets, (7) ventricular runs, (8) atrial fibrillation, (9) supraventricular ectopic beats (SVEB), (10) supraventricular bigeminy, (11) supraventricular trigeminy, (12) supraventricular quadrigeminy, (13) supraventricular couplets, (14) supraventricular runs and sinus tachycardia, and (15) sinus bradycardia. Implementing a fully automated system minimizes burden on physicians and helps them prioritize their patients thus allowing them to attend to more patients as well as speeding up diagnosis and treatment. Such systems also have the advantage that they can be easily integrated into telemedicine platforms for remote delivery of healthcare services.

To understand cardiac arrhythmias, electrocardiogram signals are acquired. In general, the electrocardiogram (ECG) is a graphical recording of the heart's electrical activity and the different phases of the heart's electrical activity are represented as different types of waveforms on the ECG and presence of arrhythmias results in morphological changes of these waveforms. Thus, ECG signal data contains rich information pertaining to the heart's functionality and provides useful insights about presence of arrhythmias. Apart from helping understand arrhythmias, the ECG also serves various other purposes such as analyzing effects of medications, evaluating cardiac injuries, monitoring heart rate, detecting ischemic damages, etc., among other things.

ECGs are obtained using electrodes that are placed in various positions and the tracing of electrical activity between a pair of electrodes is termed a lead. Different lead orientations help view the heart from different perspectives and hence provide information about different cardiac regions. Specifically, the leads help analyze the cardiac electrical activity in two planes, namely, frontal and horizontal planes. As the name suggests, the frontal planar leads look at the heart from the front of the body. There are two types of frontal leads: Standard limb leads and Augmented limb leads. The standard limb leads include Leads I, II and III while the augmented limb leads include Leads aVR, aVL and aVF. On the other hand, horizontal planar leads view the heart from the top i.e., if the human body were sliced horizontally and hence the name. This includes six chest leads, also called precordial leads, viz. V1, V2, V3, V4, V5 and V6. Each of the twelve lead orientations help capture the heart's electrical activity from a certain specific perspective.

FIG. 1 shows the primary components of an electrocardiogram, where different phases of cardiac activity manifest as different waveforms on the ECG. These waveform components primarily comprise: (1) isoelectric line; (2) P-wave; (3) QRS complex; and (4) T-wave.

The isoelectric line or the baseline represents the condition where there is no electrical activity. Deflections above and below the baseline correspond to depolarization activity depending on electrical activity towards or away from the positive electrode. The isoelectric line is used as a reference to determine the amplitude of each wave deflection and can be used to identify unusual amplitude changes such as abnormally-peaked P-waves, inverted T-waves, etc. Oftentimes, the isoelectric line is superimposed with a low frequency component which results in what is known as baseline wander.

The P-wave represents atrial depolarization of the heart. This is the first waveform manifestation of the electrical impulse generated from the SA node, which are sensed as an ECG waveform signal. Abnormal P-waves can often be a pointer to enlarged atria and unusually tall or pointed P-waves could indicate heart failure, atrial fibrillation, supraventricular ectopy, etc. Inverted P-waves often correspond to junctional ectopy.

The QRS complex is the most characteristic feature in an ECG and corresponds to the ventricular depolarization phase of the heartbeat cycle. Since ventricles have a much larger muscle area and mass compared to the atria, the QRS complex has a significantly higher magnitude and appears much larger than P-waves on the ECG. Thus, although atrial repolarization and ventricular depolarization occur almost simultaneously, atrial repolarization activity gets hidden under the larger QRS complex and is usually not visible on the ECG. As the name suggests, the QRS complex is a complex that is made up of three waveforms, viz. Q-wave, R-wave and S-wave. The Q-wave and S-wave are negative deflections from the isoelectric line The R-wave is usually the first positive deviation, after the P-wave, from the isoelectric line and the peak location of the R-wave is termed as R-peak. Under normal conditions, the QRS complex is expected to have a duration of 0.11 s or less. In reality, the QRS complex has different morphologies depending on the lead from which it is measured. In order to glean useful arrhythmia information using QRS complex information, the lead information must also be provided. For instance, often times the QRS complex may be negative in certain lead orientations such as leads V, V2, etc., owing to their orientation w.r.t to the net ventricular depolarization vector, but this is not indicative of any arrhythmia on its own. In this research, we use lead II and in lead II, under normal conditions, the QRS complex has a positive R-wave and negative Q- and S-waves. Thus, a negative QRS complex in lead II is indicative of a cardiac abnormality and would necessitate further medical investigation.

The R-peak is the most significant ECG fiducial point and is often considered to be representative of a QRS complex as a whole. The distance between consecutive R-peaks, termed as the RR-interval provides useful insights into underlying heart rate dynamics and is frequently used for evaluating an individual's cardiac health. In the present disclosure, the RR-interval information serves as the primary source of ECG information for performing arrhythmia analysis and hence accurate detection of QRS complexes is a pre-requisite for developing robust arrhythmia detection techniques.

The T-wave represents ventricular repolarization. It usually has the same deflection as that of the preceding QRS complex and hence on lead II, it appears as a positively deflected wave under normal cardiac activity. The T-wave is not perfectly symmetric with a shallower slope for the first half and a steeper slope for the second half. The offset (end) of T-wave is identified a by return to the baseline and indicates the end of one cardiac cycle i.e., a single heartbeat. In the presence of abnormalities such as premature ventricular complexes, etc., the T-wave has an opposite polarity to that of the QRS complex. Oftentimes, unusually tall T-waves might be indicative of hyperkalemia, which refers to excessive concentration of potassium (K+) in the blood. Taller T-waves can mimic QRS complexes and can affect the performance of a QRS detector. Hence care must be taken to avoid misclassifying T-waves as QRS complexes.

In the present disclosure, information from single-lead electrocardiogram (ECG) signals is utilized to create a rich set of arrhythmia-specific features to aid in the development of highly accurate arrhythmia detection models. ECG is a waveform representation of the heart's electrical activity and cardiac arrhythmias often manifest as morphological variations on the ECG.

Figure 2:
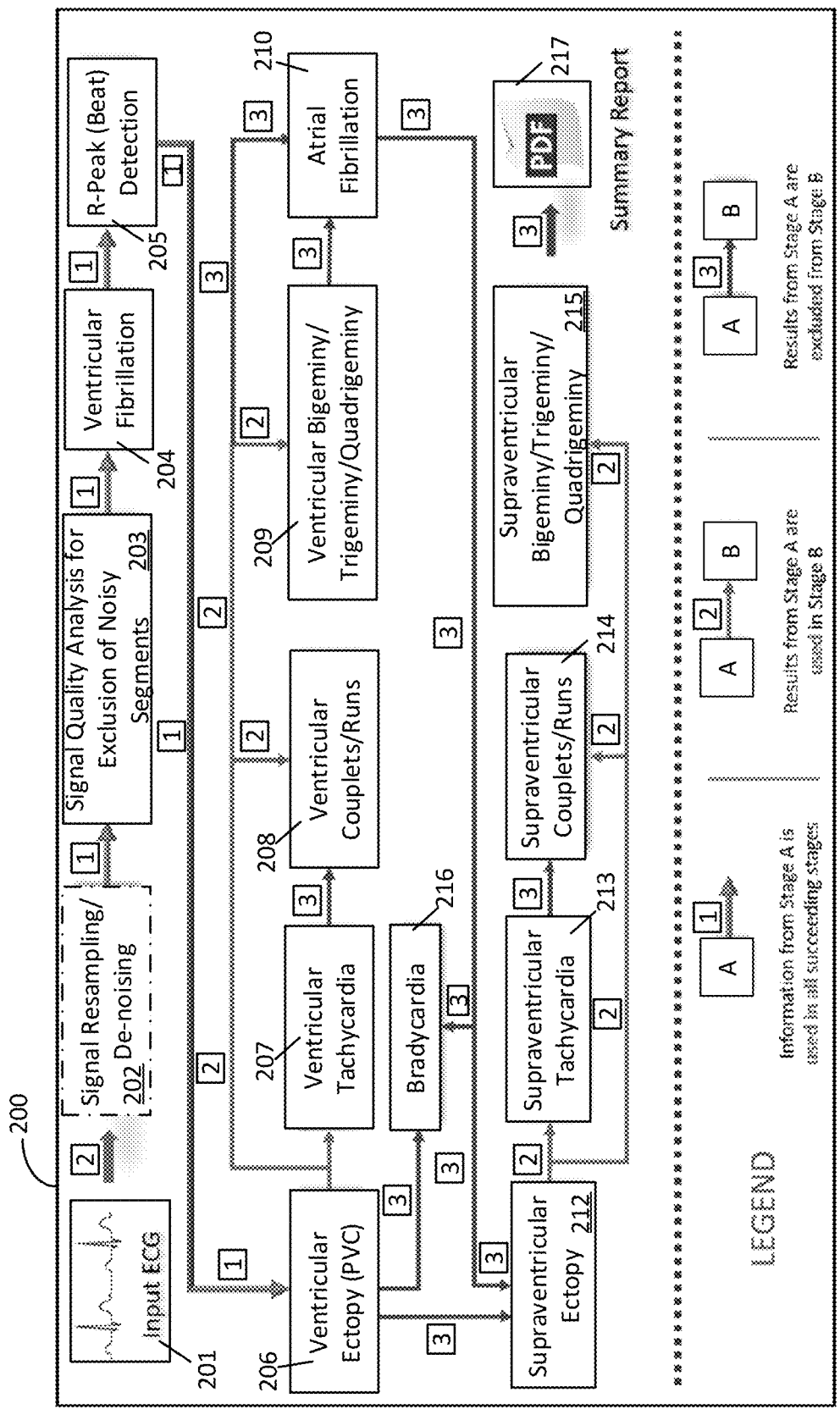
FIG. 2 is a schematic/flow diagram of an exemplary arrhythmia analysis process in accordance with embodiments of the present disclosure.

FIG. 2 is a schematic/flow diagram of an arrhythmia analysis process in accordance with embodiments of the present disclosure. In one illustrative embodiment, various steps are performed by an appropriate hardware system, embodiments of which are described further herein. An exemplary method (200) initiates with acquiring (201) an ECG signal and prior to performing any arrhythmia analysis, the incoming ECG signal is preprocessed (202) to remove low frequency and high frequency artifacts using Stationary Wavelet Transforms and Denoising Convolutional Autoencoders. This initial step is complemented by a signal quality assessment (203) using Convolutional Neural Networks where ECG segments corrupted by high grade motion artifacts are identified and suppressed from further arrhythmia analysis. Following the initial steps, the act of detection (204) of Ventricular Fibrillation and Sustained Ventricular Tachycardia which is implemented using a Random Forests classifier. Next, the act of beat detection (205) using a combination of Convolutional Autoencoders and adaptive thresholding is carried out to accurately detect R-peak locations, which is a key to performing robust arrhythmia analysis. Then, techniques for detection of PVC-beat-based ventricular arrhythmias (206, 207, 208, 209) are implemented using Semi-supervised Autoencoders combined with Random Forests and logical analysis. This step is followed by atrial fibrillation detection (210) using Markov models in conjunction with Random Forests. Finally, logical sequence analysis techniques are applied to perform acts of detecting additional SVEB based supraventricular arrhythmias (212, 213, 214, 215, 216). The results from the arrhythmia analysis are outputted (217) in the form of a user-readable ECG Analysis Report (summary report). In certain embodiments, an exemplary report contains useful information as follows: (a) Summary statement stating all the arrhythmias detected by the arrhythmia analysis; (b) Average heart rate (in bpm); (c) Number of PVCs and SVEBs; (d) Overall duration of high grade noise episodes; (e) Onset and offset of individual high grade noise episodes; (f) Overall duration of individual arrhythmias; and/or (g) Onset and offset of all episodes for each arrhythmia that is detected in the arrhythmia analysis stage.

The process steps are coded as follows. Connection lines denoted with a "1" imply that the information from a foregoing stage (or step) is used in all succeeding stages. For example, steps 204-216 all utilize the information from the first stage (steps 202 and 203). A first step (or stage) connected by a connection line denoted with a "2" to a second step utilizes results from the first step if the step indicates the arrhythmia is present. For example, step 209 utilizes results from step 206 upon positive detection of PVC in step 206. In another example, step 215 utilizes the information from steps 202, 203, 204, 205 and 212. When a connection line denoted with a "3" connects a first step (or stage) to a second step, the data from the first step is excluded from analysis in the second step if the arrhythmia is detected in the first stage. For example, step 208 does not rely upon results of ventricular tachycardia analysis in step 207, but it does rely on the ventricular ectopy (PVC) analysis of step 206. In another example, if atrial fibrillation is detected in step 210, then no further steps are performed and the process moves to the summary report and possibly an alert, if enabled. Alerts are communicated in real-time or in the report, if an alert flag is enabled for positive detection in any given step.

The arrhythmias analysis methods and algorithms of the present disclosure are device-agnostic and are well-equipped to analyze data from a diverse range of ECG acquisition devices and are suitable to being executed by diverse computing systems. In an exemplary embodiment, a cloud-based arrhythmia analysis platform, termed AutoECG, hosts the arrhythmia analysis algorithms and related processes of the present disclosure. Such an AutoECG system can be designed to handle ECG signals spanning 30 seconds to 24 hours, thus facilitating real-time analysis (wearables) as well as overnight monitoring (hospitals, bedside monitoring, etc.).

Figure 3A:
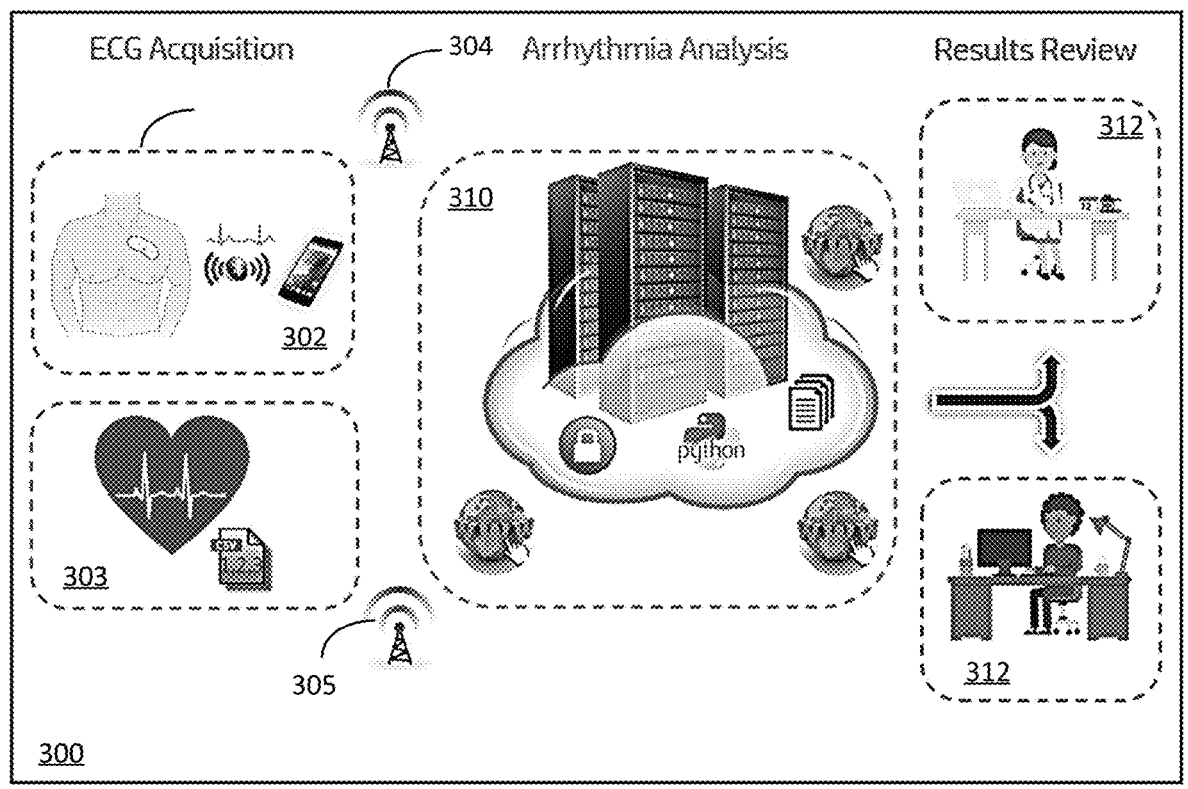
FIG. 3A is a schematic diagram of an arrhythmia analysis platform in accordance with embodiments of the present disclosure.

Referring now to FIG. 3A, an exemplary AutoECG platform 300 is shown in a schematic diagram. AutoECG platform 300 comprises an ECG acquisition components 302 and 303, an Arrhythmia Analysis component 310 and Results Review component(s) 312. AutoECG software code is deployed in the Arrhythmia Analysis component 310, which includes arrhythmia detection algorithms written in, for example, Python 3.6. The Arrhythmia Analysis component 310, including various arrhythmia analysis and detection algorithms, may be implemented (for example) on a server hardware platform as a web service, the hardware platform including (for example) a 64-bit dual-core Intell Xeonl Platinum 8175M CPU processor operating at a clock frequency of 2.50 GHz. The server can be provided by Amazon Web Services in the form of Infrastructure as a Service (IaaS).

With further reference to FIG. 3A, ECG analysis components 302 and 303 include an ECG machine (e.g. Vitalograph 12 lead ECG with Wireless Bluetooth) which acquires an ECG waveform signal over network communications 304 from a living being as is known in the art and creates corresponding ECG waveform signal data. In ECG analysis component 302, the ECG waveform signal data is communicated via a communications network to a local/client computer (e.g. using a Bluetooth network). In an exemplary embodiment, the local/client computer is a smart phone or smart watch device operating an application or "app" which is minimally configured to accept the ECG waveform data, transmit it to the web service server for arrhythmia analysis and receive results information from the server related to arrhythmia analysis. In ECG analysis component 303, the ECG waveform signal data is saved as a data file (e.g. csv text file) which is uploaded to the server over network communications 305, such as via a website from a computer operating a web browser. Results review component 312 includes, for example, the output of arrhythmia analysis results via a computer and subsequent review, such as by a physician (or other medical professional), a computer operating a web browser or an app operating on a smart phone/watch allowing the operator to communicate with the web services server, etc. For example, arrhythmia analysis results may be communicated to the physician for review via a website or via app running on smart phone/watch. The website is configured so that the operator may interactively configure the view of the results to better understand them. Results review component 312 can also include, for example, a technician, a computer operating a web browser or an app operating on a smart phone/watch allowing the operator to communicate with the web services server. The technician may interactively configure AutoECG parameters or settings based on uploaded and analyzed ECG waveforms to cause supervised learning activities within the analysis algorithms and related processes operating on the web services server. The supervised learning activities continue to improve the detection of the various arrhythmias from ECG waveforms over time.

An example ECG analysis report is presented in FIG. 3B. The report shows arrhythmia analysis results for the uploaded ECG file-tri.csv, in which the AutoECG software detects the presence of ventricular bigeminy (VBI) and ventricular trigeminy (VTRI) in the extracted ECG and this is highlighted in the ECG Analysis Summary section of the report. The Analysis Results section provides more detailed information such as processing time, ECG duration, average heart rate, arrhythmia episodes, etc. More importantly, the subsections Ventricular Bigeminy and Ventricular Trigeminy in the report provide the corresponding onset and offset timestamps for each of the VBI and VTRI episodes detected by the arrhythmia analysis algorithms along with reporting the overall time duration for each arrhythmia. It has to noted that the findings in the ECG Analysis Report should not be used in any diagnostic capacity by the user and that the user must contact a physician/medical practitioner for further review of the report.

Various modes of operation are contemplated. At least three illustrative embodiments are described as follows for Mode A, Mode B, and Mode C. Mode A provides for real-time arrhythmia detection. Accordingly, Mode A involves a continuous upload of measured waveform from ECG machine to the AutoECG web service, the AutoECG analyzing the ECG waveform and sending analysis results back to operator in real time (e.g. physician) including sending alerts if arrhythmias are detected, especially life threatening arrhythmias. Mode B provides for near real-time arrhythmia detection. Under Mode B, an ECG machine collects data, saves the data as a file, uploads the data file automatically to the AutoECG web service when measurement is complete, performs arrhythmia analysis, and sends results back to the user, which may include alerts if arrhythmias are detected. Next, Mode C involves asynchronous arrhythmia detection and results. For Mode C, an ECG machine collects data, saves data corresponding to an ECG waveform as a file which is transferred to a computer readable media (e.g. csv file on a hard drive of a computer), the computer readable media is uploaded to the AutoECG web service, the results are made available via an AUTOECG website, such that the results may be downloaded by a user, where the results may include alerts if arrhythmias are detected.

The present disclosure is not limited by hardware or by the illustrative embodiments presented above. Many modifications, such as hardware modifications and other modes of operation will be apparent to those skilled in the art without departing from the scope and principles of the described embodiments. For example, in Mode A, it is conceived that an exemplary method/system includes a smart phone app (computer program) operating on a smart phone device that manages the data transfer between the smart phone device and ECG machine and manages the data transfer between the smart phone device and the AutoECG web service. Furthermore, it is conceived that the user is able to configure certain aspects of the analysis results reporting, for example, on what thresholds should an alarm be raised or how often the app receives and displays an update from AutoECG analysis. In another embodiment, among others, the smart phone itself can be used in the place of cloud for making computations and decisions. In yet another embodiment, a Field Programmable Gate Array (FPGA) can be use in the place of a cloud for computing and decision making.

All of modes A, B and C allow for review of the AutoECG analysis results by a physician review portal on the AutoECG website, which would normally require an authenticated session in the portal. In modes A and B, where a smart phone, watch, or local/client computer is operating a computer program to automatically communicate with the AUTOECG Web service, the computer may be programmed (via the computer program) to display the portal during an authenticated operation of the program.

Modes A, B and C my further include a technician review portal wherein a person trained in operating and reading the analysis results of AutoECG oversees the analysis (real-time or asynchronous) and may provide feedback to (1) the operator and (2) to the AutoECG web service. In case (2), for example, the technician is reading the ECG waveform and the results from AutoECG, performing their own analysis, detecting any errors made by AutoECG and providing supervised learning input into programmable machine learning functions of arrhythmia analysis algorithms operating to analyze ECG waveforms. This provides real-time learning for building a more accurate model with every iteration.

In an exemplary embodiment, among others, prior to using the AutoECG platform, users are required to login using their username/password credentials. All user accounts (users, doctors, technicians, etc.) hosted in AutoECG are securely protected via Auth0 and data access is compartmentalized depending on user type and access level.

According to an exemplary embodiment, the Arrhythmia Analysis component 310 works as shown in FIG. 2 to accomplish arrhythmia analysis process 200. Accordingly, the AutoECG platform 200 accepts ECG waveform data (e.g., in the form of a single-column comma-separated values (.csv)). Upon uploading the ECG waveform date to an AutoECG (web services) server, other data or input may be specified for the AutoECG server. For example, the user can enter the sampling frequency which is used in computing heart rate metrics. Once this is completed, the ECG waveform data can be processed and ready for arrhythmia analysis arrhythmia analysis for detection of the various arrhythmias is performed as follows.

First, after acquiring or obtaining the ECG data, the data is processed to remove noise and low quality segments, as indicated by denoising or noise removal step/stage 202 and signal quality analysis step/stage 203 of FIG. 2. In particular, the electrocardiogram (ECG) signal acquisition process is subject to interference due to several factors that can often compromise the integrity of the measured signal. This includes patient movements, electrode disconnects, powerline interference, muscle noise, etc. Hence, it is imperative that the ECG signal be pre-processed for noise removal (denoising) 202 and signal quality analysis 203 prior to performing any arrhythmia analysis. There are primarily three types of artifacts that affect the quality of arrhythmia classification or any kind of ECG analysis for that matter. They are (1) low frequency noise, (2) high frequency noise, and (3) electrode motion (EM) noise.

Low frequency and high frequency noise generally occupy frequency bands that do not overlap with QRS complex frequencies and hence can be suppressed without compromising useful QRS information and fall under the category of ECG denoising while EM noise cannot be suppressed without losing valuable ECG information and can only be managed. ECG segments deemed to be too noisy i.e., corrupted to a large extent by EM noise, are omitted from further arrhythmia analysis to mitigate occurrence of false positives. The approaches required to handle the above artifacts vary for each type. The following section provides a brief review of techniques used for handling the aforementioned classes of artifacts. This is followed by a comprehensive description of the ECG denoising and noise classification methodologies implemented in the present disclosure.

Low frequency noise refers to superposition of low frequency components (usually less than 1 Hz) with the ECG signal. This results in wandering/drifting of the isoelectric line. Hence this artifact is termed as baseline wander or baseline drift. Factors causing baseline wander artifacts include patient movement, respiratory factors such as breathing, changes in electrode impedance, etc. Since the frequency range of baseline wander is usually less than 1 Hz, suppressing this artifact does not result in loss of any useful information required for analysis of the arrhythmias pertaining to the present disclosure. For ensuring reliable baseline wander removal, Stationary Wavelet Transform is used.

The most commonly used tool for spectral analysis of signals to aid in filtering operations is the Fourier transform. But the Fourier transform assumes the input signal is stationary i.e., all frequency components occur at all time instants. This, therefore, limits the application of Fourier transform to non-stationary or transient signals such as the ECG. Transient signals have different frequency components dominating different sections of the signal and hence require more sophisticated tools to perform efficient spectral analysis. The solution to this is the Discrete Wavelet Transform (DWT). DWT is a signal processing tool that provides efficient time-frequency representation of a signal. The term wavelet refers to a small wave or a template (mother wavelet) which is matched with the input signal. The template is stretched and compressed by a finite factor (usually 2) to analyze the input signal at multiple levels of resolution. Stationary Wavelet Transform (SWT) (Nason and Silverman, 1995) is a variant of DWT where there is dyadic compression in the frequency domain without any downsampling in the time domain. The wavelet coefficients therefore have the same length (duration) as that of the input at each scale which helps reduce resolution errors at higher scales (lower frequencies). The SWT step can be viewed as a means to compute the effective band-pass for the signal at each scale.

Figure 4:
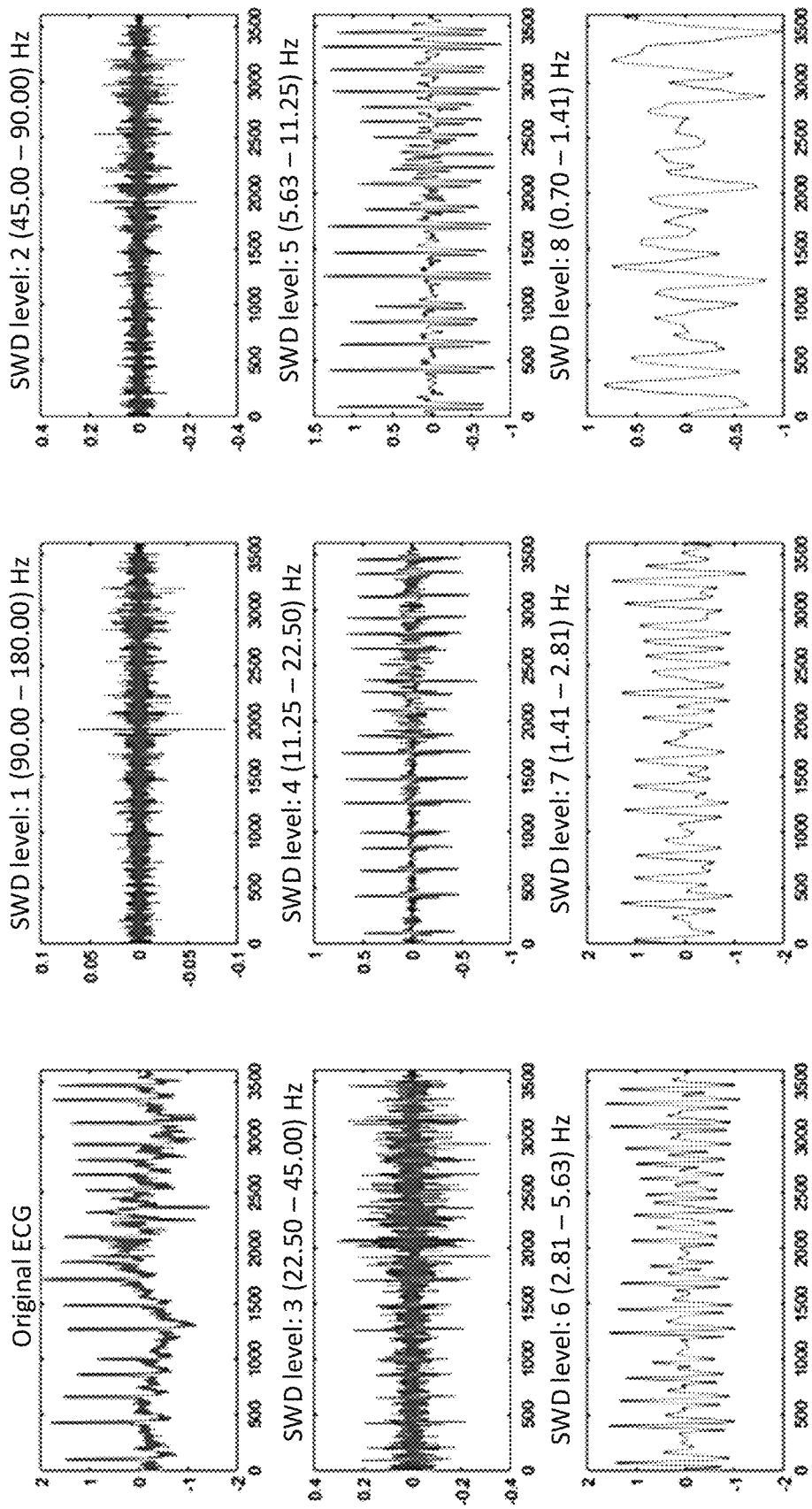
FIG. 4 is a stationary wavelet detail decomposition of an ECG signal.

The models described in the present disclosure have been trained and validated using signals sampled at 360 Hz (although other sampling frequencies may be used). Therefore, the incoming ECG signal is first resampled to a set sampling rate at 360 Hz before performing any task. Following signal resampling, SWT is applied to the signal. In the present disclosure, the Daubechies3 (Db3) (Daubechies, 1992) is used as the mother wavelet for computing SWT detail coefficients. Since the signals are resampled at 360 Hz, frequency components up to 180 Hz can be reconstructed from the SWT detail coefficients, as per Nyquist-Shannon theorem for sampling signals. Nine-level SWT is applied to the resampled signal. Owing to dyadic compression in the frequency domain, this results in the first eight levels corresponding to frequency components in the [0.7 Hz to 180 Hz], as shown in FIG. 4.

Therefore, reconstructing the signal using coefficients from only the first eight levels leads to suppression of all frequencies below 0.7 Hz. This results in removal of the major low frequency components that correspond to baseline wander artifacts. Although this does not ensure filtering out of frequencies up to 1 Hz, it must be noted that reconstructing the signal using only the first seven detail coefficients leads to suppression of frequencies up to 1.4 Hz (as a consequence of dyadic compression) and this could compromise useful ECG information. Hence the first eight levels are retained to perform efficient low frequency noise removal in the present disclosure.

High frequency (HF) noise refers to corruption of ECG signal by spectral components generally higher than 30 Hz. This makes the isoelectric line appear extremely chaotic and can often mask useful ECG fiducial markers such as the P-wave, T-wave, etc. Although the bandwidth of HF noise is outside the useful QRS complex range, it can still result in false beat detection, which can result in unreliable arrhythmia analysis. This especially significant for beat detection methods that adaptively update their thresholds, such as an exemplary embodiment of the present disclosure. Factors causing HF artifacts include powerline interference (50 Hz/60 Hz), thermal noise, muscle (EMG) artifacts, etc.

Similar to the baseline wander removal approach, HF noise can, in theory, be removed by suppressing SWT detail coefficients that correspond to frequencies 30 Hz and above. This would be equivalent to retaining only the detail coefficients from level-4 to level-8 to reconstruct the HF-noise suppressed signal. But there is an inherent disadvantage to this approach. SWT can be viewed as a sequence of band-pass filtering operations and since a band-pass filter is essentially a cascaded version of high-pass and low-pass filters, the low-pass filtering process (removing level-1 to level-3 SWT detail coefficients), results in mitigation of QRS amplitudes and makes the QRS complexes shallower and wider. In fact, any low-pass filtering technique would give rise to this type of undesired effect on the QRS complex. Although this is not a deterrent to the beat detection process itself, this can often result in a large number of false positives while performing PVC classification, as PVC beats are primarily characterized by shallower slopes and wider QRS complexes. Therefore, it is necessary to adopt an adaptive denoising technique that removes HF noise while retaining QRS complex amplitudes and its sharpness. To achieve that, a deep-learning based approach, using Denoising Convolutional Autoencoders, is part of embodiments of the present disclosure.

In accordance with embodiments of the present disclosure, a One-Dimensional Denoising Convolutional Autoencoder (1D-DCAE), is implemented to achieve robust HF noise suppression. The data for training and validating the 1D-DCAE HF-noise model is obtained from the MIT-BIH Arrhythmia Database (MITDB) (Goldberger et al., 2000; Moody and Mark, 2001). There are 48 records in total in the MITDB database and each of these records contain two-lead ECG signals. These signals are sampled at 360 Hz and are thirty minutes long in duration. ECG signals from twenty-two records belonging to the MITDB database were used to form the training data and ECG signals from another twenty-two records in the same database were used to form the validation data. Throughout the present disclosure, when using the MITDB records, ECG signals from lead MLII (Modified Limb Lead II) alone are used for analysis.

Each of the ECG signals from the MITDB records are used to prepare the training and validation data for the 1D-DCAE network as follows: First, each ECG signal is first subjected to baseline wander suppression as described previously. Second, the BW-suppressed ECG signal is then divided into non-overlapping segments, $ECG_{bw}$, each 650 ms in duration. Third, random Gaussian noise with zero mean and unit variance is added to each of these segments. This constitutes the noisy input data $ECG_{bw-ns}$ for the 1D-DCAE network. Lastly, the output for the 1D-DCAE network is the original, noise-free BW-suppressed data, $ECG_{bw}$.

The 1D-DCAE network is trained end-to-end using an Adam optimizer (Kingma and Ba, 2014) with an initial learning rate of 0.001. Mini-batch gradient descent is used to train the network with a mini-batch size of 64 and an epoch size of 200. Optimal model weights are chosen based on the accuracy obtained on the validation dataset and the weights that give the best performance on the validation dataset are used in the final model. This ensures that the 1D-DCAE network does not overfit on the training data and instead learns to extract useful ECG components from HF noise. The 1D-DCAE network with these best weights is the HF-noise suppression model, $Hfnoise_{model}$.

After the completion of training for the 1 D-DCAE network, an incoming ECG signal first undergoes resampling at 360 Hz, as part of the noise removal step 202. This is followed by baseline wander removal, as previously described as being part of the noise removal step 202. Then, in various embodiments, this signal is divided into nonoverlapping segments, each 650 ms, in duration and passed as input to the $Hfnoise_{model}$. The output of this model are the HF-noise suppressed segments. The non-overlapping denoised segments are concatenated in the same order as they were divided and the resultant one-dimensional signal is the final denoised ECG signal that is output from the noise removal step 202 to the signal quality analysis step 203 which addresses the third type of artifact, i.e., EM noise, which determines the quality or utility of the denoised signal for arrhythmia analysis. Henceforth, in the present disclosure, the terms "signal" or "input signal" refer to the denoised ECG signal unless specified otherwise.

In the signal quality assessment step 203, ECG segments with very high-grade noise artifacts are identified and suppressed from any further arrhythmia analysis. In particular, signal quality analysis is performed to reduce arrhythmia misclassifications. This refers to electrode motion (EM) noise detection in particular. EM artifacts need more attention as exaggerated presence of EM artifacts could potentially hinder accurate beat detection. EM artifacts are usually caused by severe patient movement and/or electrode displacements and often mimic QRS complexes in their morphology. These artifacts usually occupy the same spectral bandwidth as that of QRS complexes. Hence it is not a good idea to attempt to filter out EM noise as this may result in loss of actual QRS complex information as well. Instead, it is more efficient to identify (classify) ECG segments exhibiting significant EM interference and suppress further ECG analysis in these segments. The task of identifying extremely noisy segments is an important precursor to performing reliable arrhythmia analysis and in various embodiments, a One-Dimensional Convolutional Neural Network (1D-CNN) model (Goodfellow et al., 2016; LeCun et al., 1995) is used for the detection of ECG segments that are characterized by a high degree of EM noise.

The data for training the CNN model for EM noise detection is obtained from the MITDB database in a similar manner as the previous training for HF noise suppression. Since the signals in the MITDB database are relatively clean and lack any significant EM noise presence, synthetic EM noise data, available in the MIT-BIH Noise Stress Test Database (NSRTDB) (Goldberger et al., 2000; Moody et al., 1984), is added to the signals in the MITDB database to create the noisy input data. Thus, providing this information to the 1 D-CNN network, along with the ECG signal, helps the network learn to distinguish between EM noise artifacts and true QRS complexes.

In an exemplary embodiment, a process governing the generation of training and validation data is as follows. First, the raw ECG signal is denoised, and synthetic noisy ECG signals are created for SNR values of −4 dB. Second, the SWT level-4 detail coefficients are computed for this synthetic signal, and the synthetic signal is divided into M non-overlapping segments, each 10 seconds in duration (3600 samples at 360 Hz). Here M is the number of 10-second ECG segments present in the synthetic signal. Similarly, the SWT level-4 detail coefficient signal is then divided into M non-overlapping segments, each 10 seconds in duration. Next, each 10-second noisy segment is paired with its corresponding SWT-level-4 10-second segment to form a [M×3600×2] input. Lastly, steps 1 to 6 are repeated for SNR values in the set [−2 dB, 0 dB, 2 dB, 4 dB]; and steps 1 to 7 are repeated for all signals in the MITDB database.

The above data preparation process results in a data matrix Dem of size K×3600×2, where K is the total number of 10-segments obtained as a result of the synthetic data generation process. In the present disclosure, the value of K is 19800 with 9900 examples belonging to the training set and 9900 examples belonging to the validation set. The data examples in Dem that belong to the training set are used to train the CNN model while examples belonging to the validation set are used to determine optimal network weights that aid in robust EM noise classification. The network is trained using backpropagation and Adam optimizer with initial learning rate of 0.005. A Rectified Linear Units (ReLU) activation function (Goodfellow et al., 2016) is applied to the hidden layers while a softmax activation function is applied to the output layer. A mini-batch gradient descent is used for updating network weights with a mini-natch size of 64 and L2-regularization with a regularization coefficient of 0.01 is applied to the hidden layers (except MaxPooling layers) to reduce overfitting.

Table I shows the performance of the 1D-CNN EM noise classification model on the training and validation datasets in terms of Sensitivity (Se), Positive Predictive Value (PPV) and F-Score (Fsc). The equations for these metrics are given in Equations (1) through (3):

$$Se = \frac{TP}{TP+FN} * 100 \qquad (1)$$

$$PPV = \frac{TP}{TP+FP} * 100 \qquad (2)$$

$$F1 = \frac{2*TP}{(2*TP)+FP+FN} * 100 \qquad (3)$$

where TP refers to the True Positives i.e., correctly classified noisy segments, FP refers to False Positives i.e., clean segments misclassified as noise and FN refers to False Negatives i.e., noisy segments that are misclassified as being clean.

TABLE I

| Dataset | Se | PPV | F1 |
| --- | --- | --- | --- |
| MITDB-DS1 (Training dataset) | 99.69% | 99.94% | 99.82% |
| MITDB-DS2 (Validation dataset) | 99.61% | 99.59% | 96.60% |

Along with class labels, the 1D-CNN classifier also outputs prediction probability for each 10 s segment. This can be interpreted as the confidence with which 1D-CNN network makes a prediction (noisy or clean). Usually segments with score greater than or equal to 0.5 are classified as noise and those with scores less than 0.5 are classified as clean. In the present disclosure, segments with scores exceeding 0.9 (high probability i.e., extremely noisy) are considered to be of poor quality and are hence omitted from further analysis. FIG. 5 provides the confusion matrix information for EM classification performance on the validation dataset. In this figure, the rows (upper case NOISY and CLEAN) represent the true labels and the columns represent the predicted labels (lower case noisy and clean).

Upon completion of the signal quality analysis step 203, the stage for detection of ventricular fibrillation/sustained ventricular tachycardia (VF/VT) 204 can commence. Since this step/stage does not require beat detection, it may be performed prior to the beat detection step 205. In accordance with embodiments of the present disclosure, beat-independent arrhythmias, such as ventricular fibrillation and sustained ventricular tachycardia, can be detected using time-domain and feature-domain features along with SWT analysis using a Random Forests classifier to achieve accurate VT/VF detection performance. Additional descriptions for such techniques are provided in later sections of the present disclosure in association with the discussions of other ventricular arrhythmia detection techniques, such as those involving beat-dependent arrhythmias.

Accordingly, beat detection is vital to the field of automated cardiac monitoring and acquires further importance in the context of cardiac arrhythmia detection. Accurate beat detection techniques using QRS complex information from electrocardiogram (ECG) signals result in useful heart rate variability analysis that subsequently leads to accurate detection of cardiac arrhythmias and other abnormalities. This gains special significance in today's world dominated by non-invasive wearable ECG sensors for real-time cardiac monitoring outside of hospitals and other emergency care centers. These sensors are worn by individuals on a continual basis while performing day-to-day activities. Therefore, there is a high probability that the signals obtained from these sensors are corrupted by external noise, thereby rendering the beat detection process error-prone and thus cumbersome. This external noise can be attributed to, but not limited to, artifacts due to movements necessitated by an individual's routine activities, sensor disconnects, wireless signal transmission interference, baseline wander, powerline interference, muscle movements, etc., resulting in corruption of vital ECG information. Hence, it is necessary to develop arrhythmia analysis techniques that perform well in such scenarios with minimal false detections. Secondly, it is extremely vital that such techniques can adapt to varying heart rates exhibited by various cardiac arrhythmias when present. In the presence of arrhythmia, the heart rate is not constant and keeps fluctuating depending upon the type, severity and the number of concurrently occurring arrhythmias. Given these factors, it is imperative that beat detection algorithms and related processes are extremely robust to noise without compromising on detection accuracy, especially under arrhythmic conditions.

As previously mentioned, the QRS complex is the most significant fiduciary point in an ECG and the R-peak (peak of R-wave) is often used as a representative marker for the QRS complex as a whole. Hence, an exemplary QRS detection algorithm focuses on detecting these R-peak locations accurately. To achieve this, a combination of Convolutional Autoencoders (CAEs) and adaptive thresholding is used in a two-stage approach. Combining CAEs with a simple number of adaptive parameters enables the QRS detection algorithm to robustly detect QRS complexes in the presence of noise as well as in the presence of arrhythmias. The performance of the QRS detection algorithm was evaluated on the MIT-BIH Arrhythmia database (MITDB) and St. Petersburg 12-lead INCART database (INCARTDB) (Goldberger et al., 2000; Moody and Mark, 2001). It must be noted that the terms QRS complex, R-peak and beat will be used interchangeably throughout the present disclosure and they all refer to the R-peak location in general.

Prior to performing any beat detection, signal pre-processing and ventricular fibrillation detection are implemented to minimize false beat detections. Following this, detection of QRS complexes is carried out in a two-stage process. The first stage involves the use of a One-dimensional Convolutional Autoencoder to extract potential QRS complex locations. These locations may, at times, include ECG components that are not QRS complexes but mimic them closely such as unusually tall T-waves, voltage spikes, etc. To avoid mislabeling these components as R-peaks, an adaptive thresholding approach is adopted which forms the second stage. These two stages are briefly explained in the following discussions.

In the first stage, the denoised ECG signal is first divided into non-overlapping ten-second segments. Each of these segment is scaled in the [−1, 1] range. This results in the creation of a ECG data matrix X of size N×3600 where N is the number of non-overlapping ten-second segments in the ECG signal and 3600 represents ten seconds of ECG data at 360 Hz sampling frequency. Thus, the ith row in this matrix corresponds to the ith (non-overlapping) ten-second ECG segment in the input signal. This matrix is then fed as input to a One-dimensional Convolutional Autoencoder (1D-CAE) network, termed the beat extraction network, whose architecture is shown in FIG. 6.

The 1D-CAE beat extraction network is trained in a manner similar to a Denoising Convolutional Autoencoder, as previously described. ECG signals from the MIT-BIH Arrhythmia Database (MITDB) are used to the train and validate the learnt model. The MITDB database contains 48 ECG records in total. Each record consists of two-lead ECG signal data sampled at 360 Hz and signal from each lead is thirty minutes long in duration. ECG data from MLII lead is used for training and validating the 1D-CAE beat extraction model.

Figure 6:
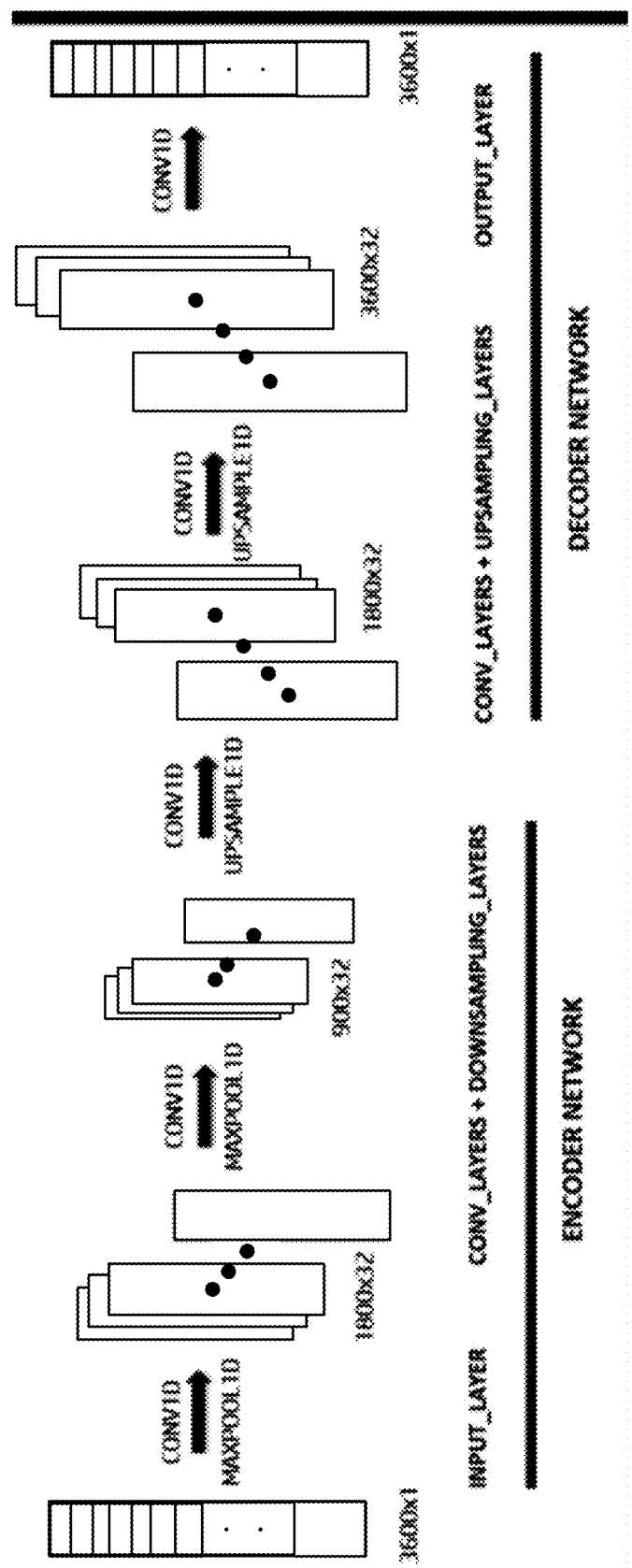
FIG. 6 shows a convolutional autoencoder network architecture for initial beat extraction in accordance with various embodiments of the present disclosure.

As can be seen in FIG. 6, the input and output layers of the 1D-CAE network each have 3600 nodes, corresponding to 3600 samples of ECG data. Hence for an input data matrix X of size N×3600, this network outputs an output data matrix Y of size N×3600. Rectified Linear Units (ReLU) activation is applied to each node in each of the four hidden layers (two hidden layers in the encoder network and two hidden layers in the decoder network). On the other hand, hyperbolic tangent function is applied to each node in the output layer so that the output node values are constrained in the range [−1, 1]. Mean squared error (mse) is used as the loss function to be minimized and gradient-descent based optimization is carried out using the Adam optimization function with an initial learning rate of 0.001. The network is trained to read an input denoised ten-second ECG segment and learn to copy potential QRS complex samples (in the input) to the output while suppressing (zeroing out) the amplitudes of other ECG components. While the training set examples are used for updating the network parameters, the validation set examples are used to evaluate the model after every parameter update and the network parameters that give the least loss on the validation data set are chosen as the optimal network parameters. The 1D-CAE model with these optimal parameters constitutes the optimal beat extraction model and is labeled beat$_{model}$. The output from beat$_{model}$ is used in stage two for implementing adaptive thresholding in order to minimize false beats and missed beats.

Figure 7:
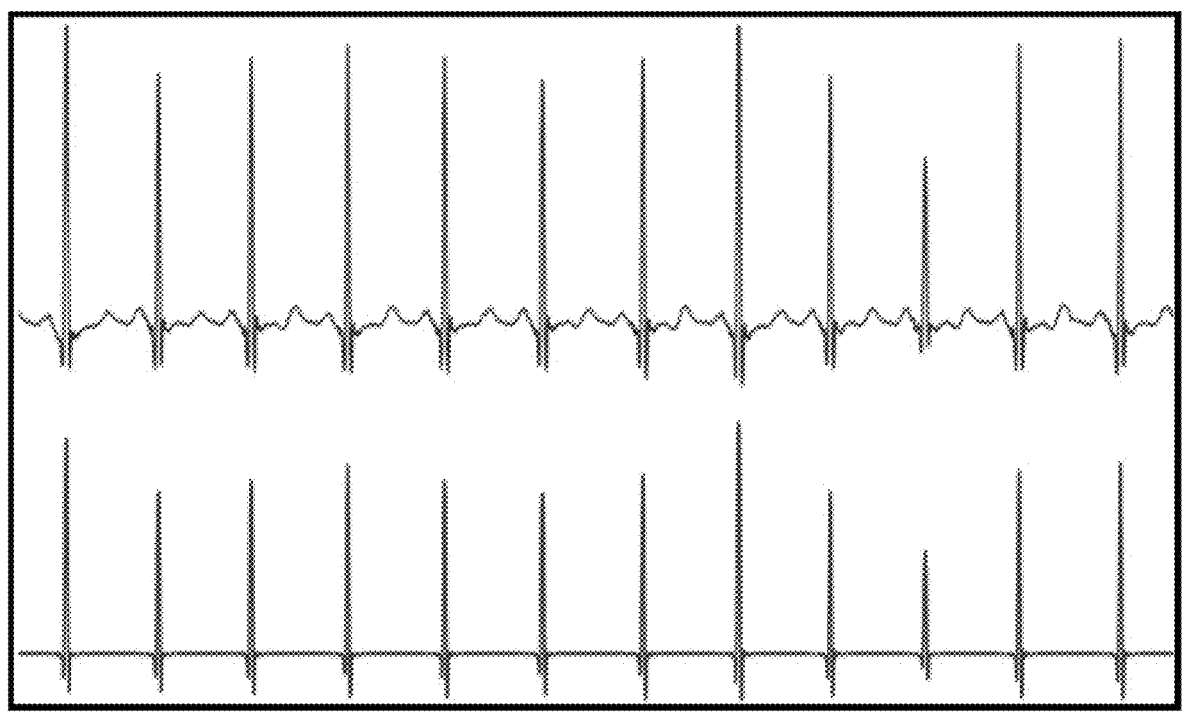
FIG. 7 shows an input and output ECG waveforms to an exemplary 1 D-CAE beat extraction model in accordance with various embodiments of the present disclosure.

FIG. 7 shows an example depicting the input and output of the 1D-CAE beat extraction network. The top of the figure shows an input ten-second denoised ECG segment and the bottom shows the output of the model. It can be seen that only QRS complexes (tall peaks) are copied to the output while other ECG components such as P-waves and T-waves are essentially nullified in the output.

Following beat segmentation in the previous section, adaptive thresholding is implemented to accurately identify beat locations (indices) and minimize occurrence of false beats and missed beats in the second stage. The output matrix Y from beat$_{model}$ consists of N ten-second beat vectors with potential QRS complexes enhanced and other ECG components suppressed. From each for these vectors, the corresponding R-peak locations must be detected while being robust to noise and simultaneously being able to identify low amplitude true beats. The adaptive thresholding stage is implemented to achieve these two goals. The adaptive thresholding stages consists of five major phases: (1) Initial peak detection; (2) Missed beat detection; (3) False beat removal; (4) Threshold update; and (5) Final R-peak location update. Before delving into details about the five phases, some useful initializations and definitions are presented below in an illustrative implementation:

1. Fs: Sampling frequency of the denoised ECG signal, i.e., 360 Hz (since all signals are resampled at 360 Hz prior to signal pre-processing).
2. pk_thr: R-peak threshold–Minimum R-peak amplitude threshold for identifying potential R-peaks. Initialized to 0.25 for learning stage.
3. rr_thr: RR-interval threshold–Minimum RR-interval threshold between two consecutive R-peaks. Initialized to (0.25*Fs) samples, i.e., 250 milliseconds for learning stage since physiological constraints require two heartbeats to be spaced at least 250 milliseconds from each other temporally.
4. missed_thr: Minimum separation threshold between consecutive peaks for identifying missed beats.
5. temp_locs: Vector storing temporary peak locations (indices) for the current beat vector.
6. pk_vec: Vector storing peak amplitudes for the current beat vector.
7. ppi_vec: Vector storing peak-to-peak intervals for the current beat vector.
8. ecg_locs: Initial empty vector for storing actual R-peak locations.

The first phase of the adaptive thresholding stage concerns initial peak detection. In various embodiments, an exemplary implementation of the first phase involves (1) scanning the ten-second beat vector to identify peak locations with minimum amplitude of pk_thr units and separated by at least rr_thr samples; (2) updating temp_locs with locations of above found peaks; (3) updating pk_vec with amplitudes of these peaks; and (4) updating ppi_vec with peak-to-peak interval (PPI) values computed from these peaks. It is noted that PPI values are simply the successive difference values between peak locations (indices).

The second phase of the adaptive thresholding stage concerns missed beat detection. In various embodiments, an exemplary implementation of the second phase involves (1) determining interval values from ppi_vec which exceed a predefined threshold, missed_thr; (2) scanning each interval found in step 1 for peaks with a minimum amplitude of 0.05 units; and (3) updating temp_locs, pk_vec and ppi_vec vectors appropriately with the new peaks found in the previous step. For step (1) of the second phase, the internal value can be computed as follows:

if (i=1):

$$\text{missed\_thr} = (1.5 * Fs) \qquad (4)$$

else:

$$\text{missed\_thr} = (1.5 * ppi\_thr) \qquad (5)$$

Equation (4) corresponds to the learning stage i.e., the first ten-second beat vector (hence, l=1). Equation (5) corresponds to the remaining beat vectors (i.e., l>1).

The third phase of the adaptive thresholding stage concerns false beat removal along with detecting actual QRS complexes, since the above described missed beat detection phase might have detected peaks that may not correspond to true QRS complexes. These include tall T-waves, voltage spikes, trivial EM noise peaks, etc. and are collectively termed false beats. To minimize such false beat detections, an exemplary implementation of the third phase involves (1) determining interval values from ppi_vec which are smaller than a predefined threshold, falsebeat_thr; (2) for the intervals found in the previous step, obtaining the corresponding pair of peak indices and peak amplitudes (since each peak-to-peak interval is computed from a pair of peaks) for each interval from temp_locs and pk_vec respectively; (3) for each pair of peak indices and peak amplitudes obtained in the previous step, retaining the peak index with the higher peak amplitude and delete the other one; and (4) updating temp_locs, pk_vec and ppi_vec vectors accordingly. For step (1) of the third phase, the internal value can be computed as follows:

if (i=1):

$$\text{falsebeat\_thr} = (0.33 * Fs) \qquad (6)$$

else $$\text{falsebeat\_thr} = (0.35 * ppi\_thr) \qquad (7)$$

Equation (6) corresponds to the learning stage i.e., the first ten-second beat vector (hence, l=1). Equation (7) corresponds to the remaining beat vectors (i.e., l>1).

The fourth phase of the adaptive thresholding stage concerns updating thresholds. In various embodiments, an exemplary implementation of the fourth phase updates rr_thr and pk_thr thresholds to be used for the next successive beat vector as follows:

RR-interval threshold update $$rr\_thr = \max((0.25*Fs), 0.5*(rr\_thr) + 0.5*(\text{median}(ppi\_vec))) \quad (8)$$

R-peak threshold update $$pk\_thr = 0.5*(\text{median}(pk\_vec)) \quad (9)$$

The fifth phase of the adaptive thresholding stage concerns updating R-peak locations after undergoing missed beat detection and false beat removal. In various embodiments, an exemplary implementation of the fifth phase appends the updated locations to the ecg_locs vector.

Figure 8:
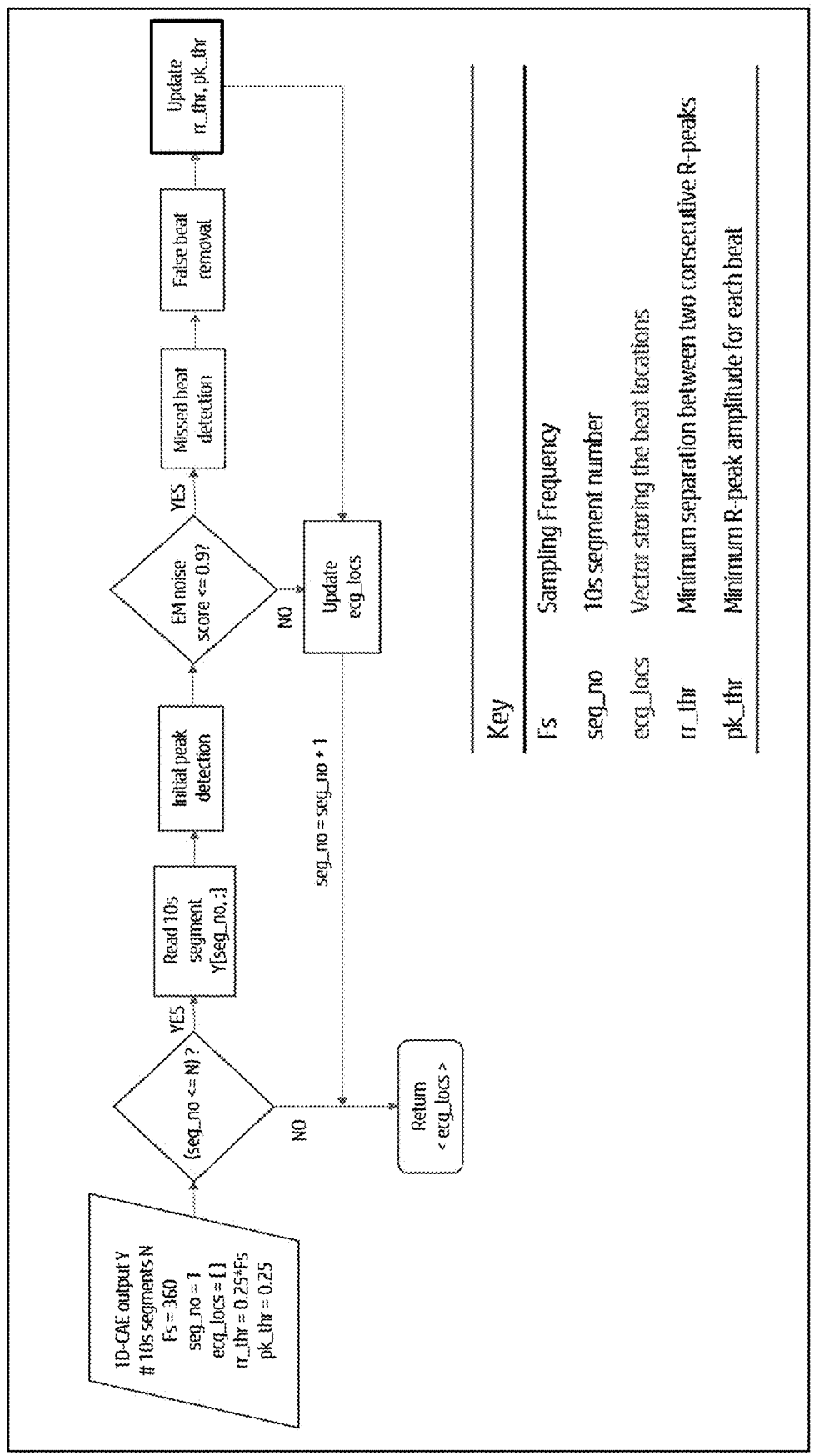
FIG. 8 shows a flow diagram depicting an exemplary adaptive thresholding stage in accordance with various embodiments of the present disclosure.

Accordingly, in an exemplary implementation, each of the above five phases are successively applied to each ten-second beat vector in Y (output from $beat_{model}$), using thresholds from the preceding cycle. The first ten-second beat vector is considered to be the learning stage that aids in learning the average RR-interval and R-peak thresholds for the ECG signal (since different individuals have different heart rates). It is important to note that if a ten-second beat vector's corresponding ten-second input ECG segment had been classified as too noisy i.e., had been assigned an EM noise classification score greater than 0.9, then missed beat detection, false beat removal, and threshold update phases are omitted for that particular beat vector. A flow diagram concisely depicting an exemplary adaptive thresholding stage is shown in FIG. 8.

Figure 9:
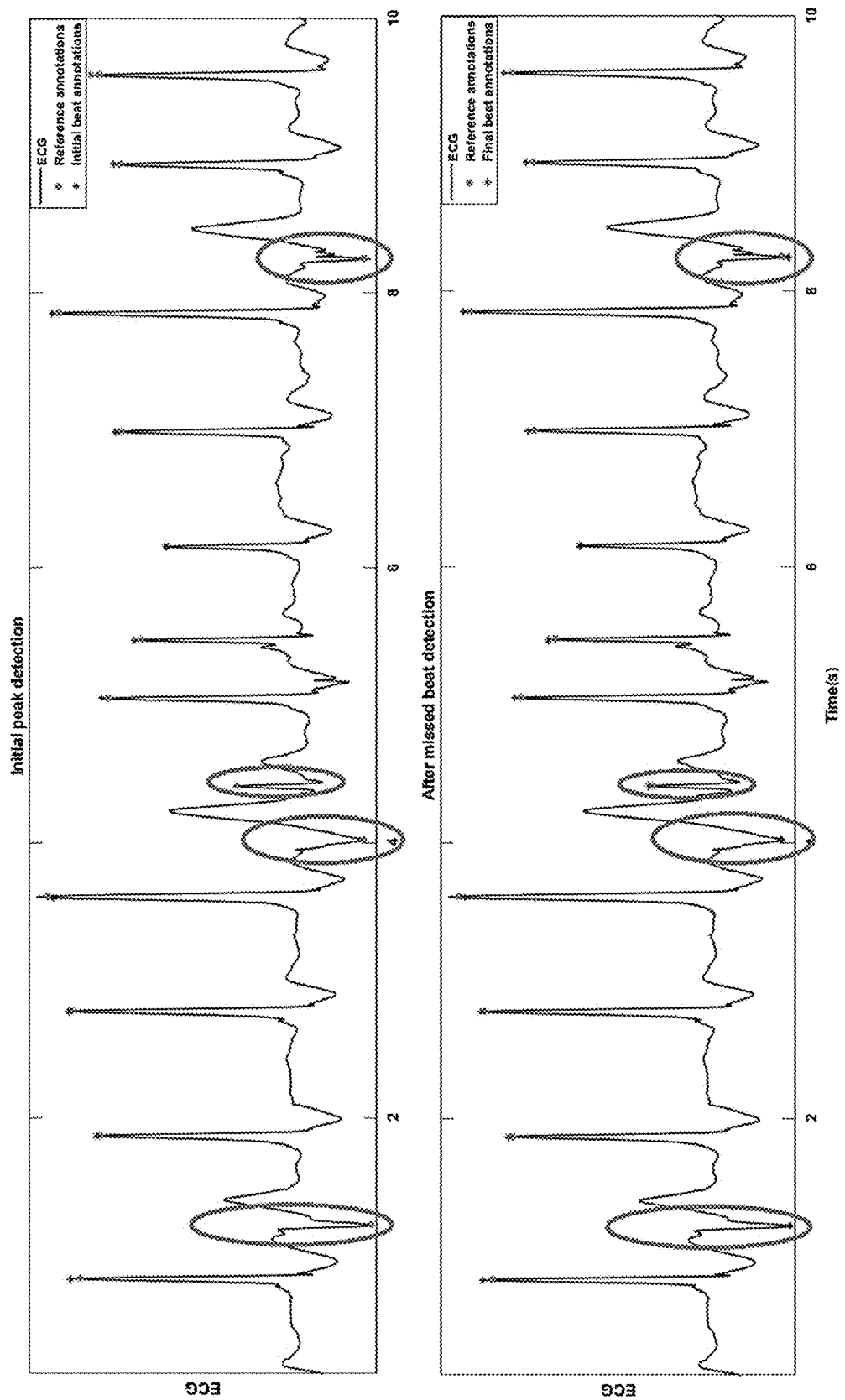
FIG. 9 demonstrates exemplary beat detection techniques with the top portion showing an initial peak detection and the bottom portion showing final beat locations after missed beat detection in accordance with various embodiments of the present disclosure.

The above described QRS complex detection techniques were evaluated on the MITBIH Arrhythmia database (MITDB), the St. Petersburg's 12-lead INCART Database (INCARTDB), and the MIT-BIH Atrial Fibrillation Database (AFDB). There are 48 two-lead ECG records in the MITDB database, with the ECG signals sampled at 360 Hz. Similarly, the INCARTDB database contains 75 twelve-lead ECG records, with the ECG signals sampled at 257 Hz. THE AFDB database on the other hand is a long-term monitoring database and contains 23 two-lead ECG records, sampled at 250 Hz and signal in each lead is approximately 10 hours long in duration. Since the present disclosure involves developing arrhythmia detection methods using information from single-lead ECGs, signals from MLII lead for the MITDB database, Lead V for the INCARTDB database and lead ECGI for the AFDB database were used resulting in 109494 beats for the MITDB records, 175906 beats for the INCARTDB records and 1090874 beats for the AFDB records. The QRS complex detection techniques (also referred to as a beat detection algorithm) achieve a sensitivity of 99.63% and a positive predictive value (PPV) of 99.88% on ECG records in the MITDB database, while achieving a sensitivity of 99.53% and PPV of 99.61% on the INCARTDB ECG records. For ECG records in the AFDB database, the beat detection algorithm achieves a sensitivity of 99.48% and a PPV of 97.35%. Although the AFDB database is not a widely used database to report QRS detection performance, it plays a significant role in the context of the work presented in the present disclosure. ECG signals in the AFDB database contain a large number of atrial fibrillation episodes which are most prominently characterized by irregular heart rate changes i.e., randomly changing RR-interval values. Hence techniques for detection of QRS complexes (or R-peaks) in the presence of atrial fibrillation must be highly adaptive to these random RR-interval transitions. The beat detection algorithm presented in the present disclosure satisfies this requirement very well as evidenced by the accuracy values shown in Table II (below), thus guaranteeing efficient performance under rapidly changing heart rate conditions which is often indicative of arrhythmias. FIG. 9 shows an example demonstrating beat detection by the disclosed approach. It can be seen that the initial peak detection step misses four beats (in ellipses). These are identified during the missed beat detection stage, thus ensuring that all the beats are detected correctly. In fact, the beats missed in the initial peak detection are premature ventricular complexes (PVCs), an abnormal beat whose detection is vital.

TABLE II

| Database (Sampling frequency) | Total beats | Se | PPV | Mean error (# of samples) |
|---|---|---|---|---|
| MITDB (360 Hz) | 109494 | 99.63% | 99.88% | 5.03 ms (<2 samples) |
| INCARTDB (257 Hz) | 175906 | 99.53% | 99.61% | 8.00 ms (~2 samples) |
| AFDB (250 Hz) | 1090874 | 99.48% | 97.35% | 12.70 ms (<4 samples) |

Figure 10:
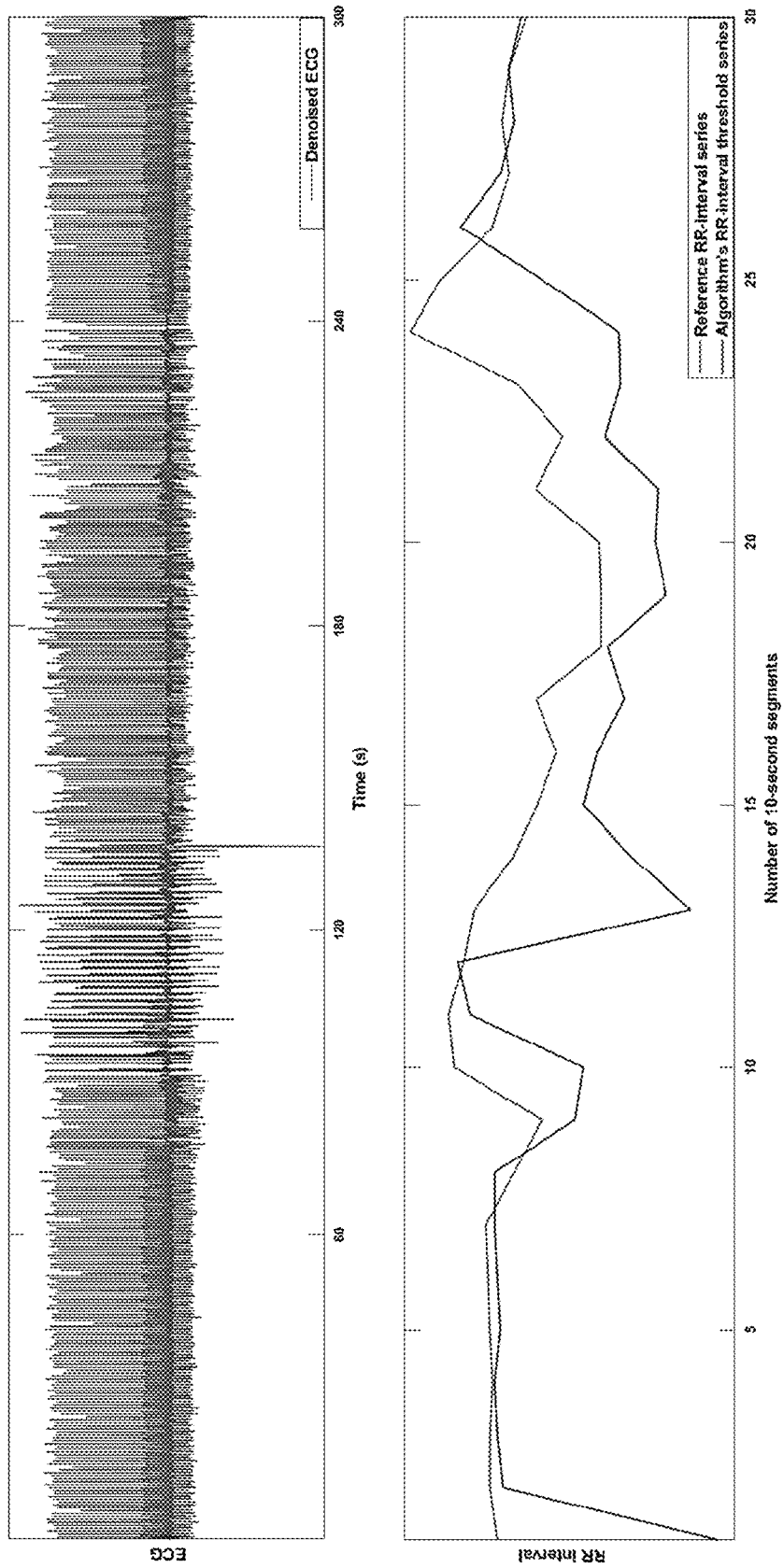
FIG. 10 demonstrates an exemplary technique for adaptive learning of RR-interval changes in accordance with various embodiments of the present disclosure.
Figure 11:
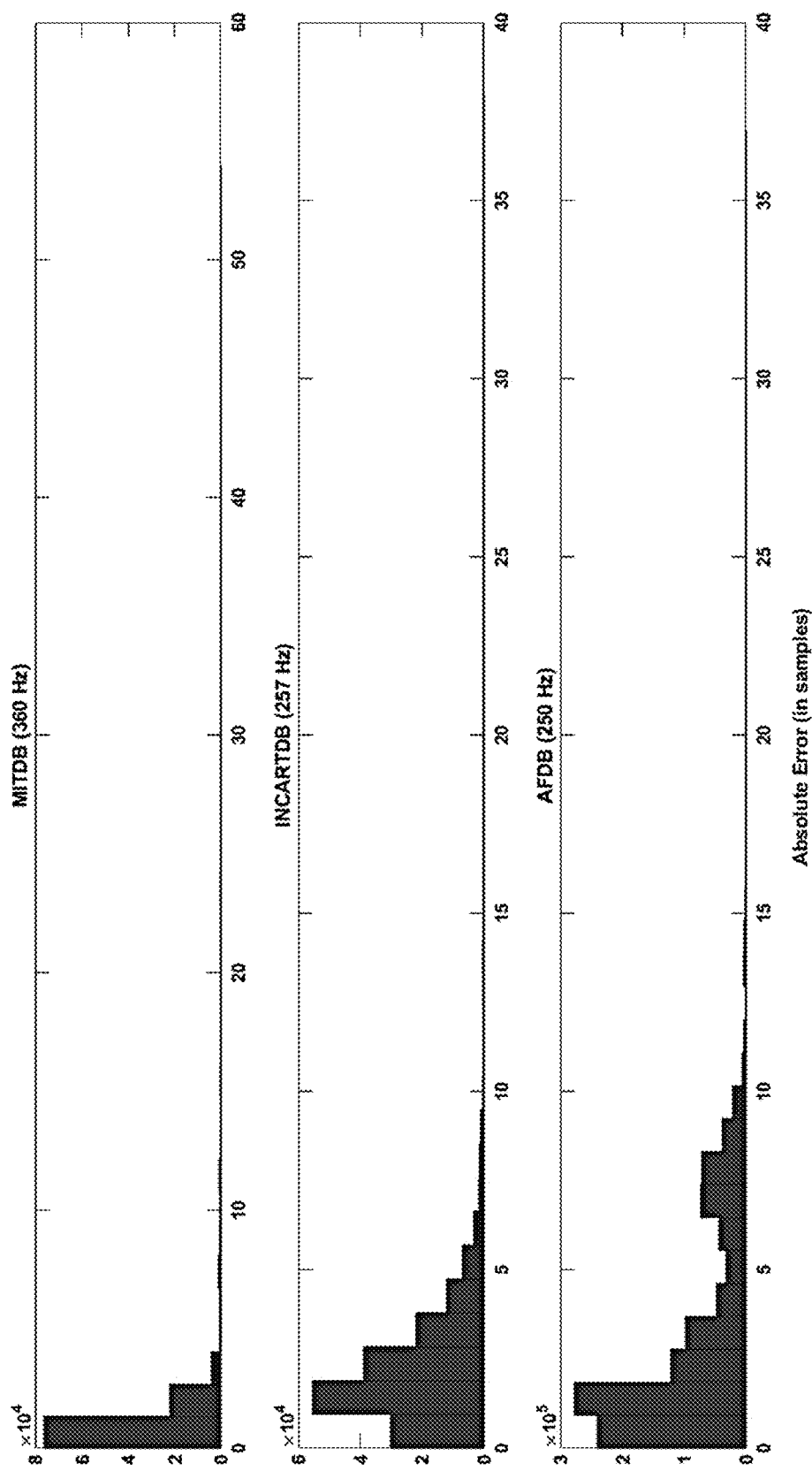
FIG. 11 shows histograms depicting the absolute error in detection of beats for each database in accordance with various embodiments of the present disclosure.

FIG. 10 shows an example of the beat detection algorithm effectively adapting to varying RR-interval values. The top plot shows a five-minute ECG segment and the bottom plot shows the true RR-interval series and the algorithm's adaptively learnt RR-interval thresholds. The ECG segment has an atrial fibrillation episode from around the 90 s mark to about 240 s. Correspondingly the RR-interval values vary irregularly in the bottom plot (labeled as Reference RR-interval series). It can be seen that the beat detection algorithm's learnt RR-thresholds (labeled as Algorithm's RR-interval threshold series) track the true RR-interval values and are almost always lower than the true RR-intervals. This ensures that the beat detection techniques maximize detection of true R-peaks while missing only very few, if any, of them. The last column in Table II shows the mean absolute error between the true R-peak locations and algorithm detected R-peak locations. It can be seen that this error is about two to four samples for all the three databases. FIG. 11 shows the histograms depicting the absolute error for beats belonging to the three databases. Each of these databases contains a combination of ventricular and supraventricular dysrhtyhms and the beat detection algorithm continues to function accurately under these conditions, thus demonstrating its ability to adapt to different types of arrhythmias.

Thus, in accordance with various embodiments, the act of beat detection (205) can be performed by a combination of one-dimensional convolutional autoencoders and adaptive thresholding to achieve accurate results in the presence of noise as well as under different arrhythmic conditions. Correspondingly, upon completion of the beat detection stage 205, the stages for the analysis of beat-dependent ventricular arrhythmias (206, 207, 208, 209) can commence.

In general, ventricular arrhythmias refer to cardiac rhythms that originate in the ventricles. The ventricles may generate electrical impulses either (i) as a consequence of irritable sites that can result in premature beats or due to Sino-atrial (SA) node failing to discharge impulses or impulses from the SA node not getting conducted properly/getting blocked completely. The former category of beats is labeled Premature Ventricular Complexes (PVCs) and the latter is termed Ventricular Escape beats. The electrical impulses can be sensed as an ECG waveform signal via an ECG machine.

Figure 12:
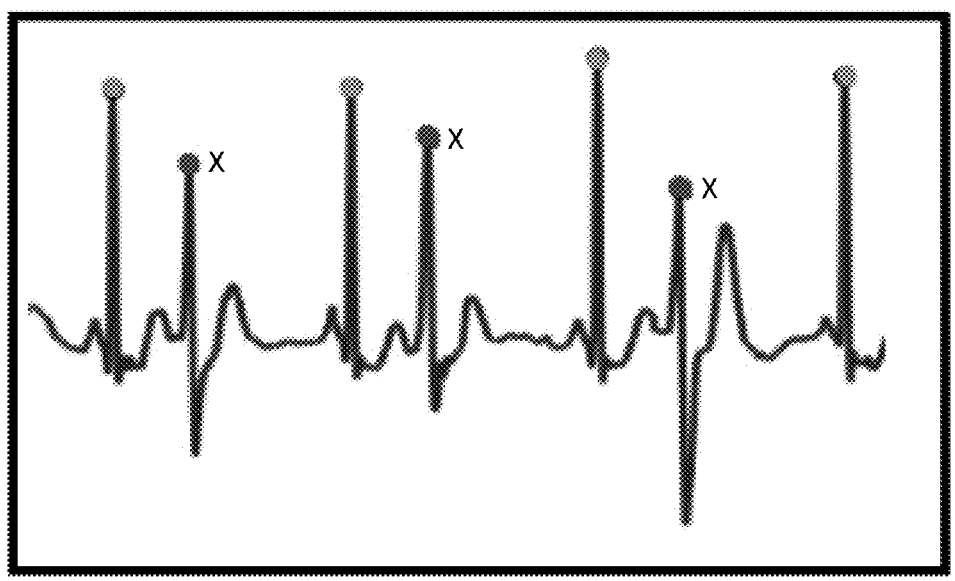
FIG. 12 demonstrates an example of Premature Ventricular Complexes (PVCs), where the markers with an x indicate PVCs.

Premature Ventricular Complexes (PVCs) are ectopic heart beats that occur as a consequence of electrical impulses originating from ventricles rather than the Sino-Atrial (SA) node. Under normal conditions, electrical impulses originate from the SA node and are propagated through the heart via the atria, atrio-ventricular node, Purkinjee fibres and the ventricles. This represents one cardiac cycle or one heartbeat. In the presence of PVCs, these impulses abnormally originate from irritable sites in the ventricles instead. This results in premature and abnormal heart beats that disrupt normal sinus rhythm. PVCs can be distinguished from other beats based on their QRS morphology on electrocardiogram (ECG) signals. In terms of their manifestation on ECGs, PVCs are characterized by wider QRS complexes (exceeding 0.12 s) with T-waves having an opposite polarity to that of the QRS complex along with absence of P-waves. PVCs are impulses that originate in the ventricles and therefore atrial depolarization does not take place which explains the absence of P-waves. PVCs can be uniform or multiform, as shown in FIG. 12, in their appearance, depending on the origin of electrical impulse discharge in the ventricles. In the figure, the markers with an x indicate PVCs. Thus, it can be seen that the first two PVCs are of similar morphology (uniform PVCs) and the third one has a different morphology compared to the first two (multiform PVCs).

Uniform PVCs refer to PVCs that originate from the same irritable site in the ventricles. On the other hand, multiform PVCs occur due to impulses being discharged from several irritable sites in the ventricles. PVCs are often followed by a compensatory pause but this is not a strict condition. PVCs can occur in healthy individuals as well as in individuals with structural heart disease. PVCs can often devolve into life-threatening conditions such as ventricular tachycardia (VT) and ventricular fibrillation (VF) and can potentially lead to heart failure if left untreated. The American Heart Associate Heart Disease and Stroke Statistics—Update 2015 reports that about 23% of out-of-hospital cardiac arrests exhibit an initial rhythm of VF or VT. Therefore, timely and accurate detection of PVCs assumes vital importance in the context of cardiac arrhythmia analysis.

The ventricular arrhythmias discussed in the present disclosure can be classified into two groups, namely, beat-independent ventricular arrhythmias and beat-dependent ventricular arrhythmias. The former group refers to arrhythmia conditions which do not require beat detection while the latter group includes arrhythmias that have beat detection as a prerequisite step. Beat-independent Ventricular Arrhythmias include Ventricular Fibrillation and Sustained Ventricular Tachycardia, whereas Beat-dependent Ventricular Arrhythmias include Premature Ventricular Complexes, Ventricular Couplets, Ventricular Runs, Ventricular Bigeminy, Ventricular Trigeminy, and Ventricular Quadrigeminy.

Ventricular Fibrillation (VF) is a subclass of ventricular arrhythmias that is characterized by chaotic or fibrillatory cardiac activity. The heart is essentially quivering in the presence of VF and is unable to pump blood effectively. There is an absence of pulse and no discernible ECG features such as P-wave, QRS complexes, T-waves, etc. are present. The lack of useful of features is the reason VF detection has been categorized as a beat-independent approach here. On the ECG, they appear as oscillatory waveforms with frequency of about 5 Hz (i.e., nearly 300 bpm—too high to effectively pump blood). Several factors can cause VF and this includes acute coronary syndromes, hypertrophy, severe cardiac failure, adverse effects of medications, external factors such as electrocution, etc. On the other hand, Sustained Ventricular Tachycardia (VT) refers to rapid occurrence of PVCs, at a rate between 150 bpm to 250 bpm, usually for more than 30 s. Sustained VT is often a precursor to VF and at high heart rates, QRS complexes and other waveforms are often not clearly distinguishable on the ECG. Depending on the morphology of PVCs, VT episodes may be monomorphic (consecutive PVCs with same shape and amplitude) or polymorphic (consecutive PVCs with varying shape and amplitude). Sustained VT can often indicate presence of myocardial ischemia. Both sustained VT and VF are shockable rhythms and hence defibrillation is the most commonly adopted approach for treating individuals with sustained VT and VF. Both sustained ventricular tachycardia and ventricular fibrillation, when left undetected or untreated, can devolve into asystole and pulseless electrical activity which are a non-shockable rhythms and even a defibrillator may not be helpful in these circumstances. Hence early detection of sustained VT and VF is very much necessary to increase the individual's chance of survival.

For the detection (204) of Ventricular Fibrillation and Sustained Ventricular Tachycardia, a machine learning model using Random Forests (RF) can be utilized in various embodiments. In such embodiments, the features that act as input to the RF classifier include both time-domain and feature-domain features.

Random Forests is a machine learning algorithm that involves growing an ensemble of binary decision trees for performing regression/classification. Decision tree models generally suffer from high-variance and thus averaging out predictions from multiple decision trees, each with the same variance, leads to a decrease in overall variance. The process of growing these decision trees is based on bagging (bootstrap aggregation), which is a technique for reducing the variance of an estimated prediction function. Here, bagging primarily involves creating several data subsets from the training data by random subsampling with replacement. Each of these data subsets is then used to train a decision tree model separately. Additionally, for each tree, only a random subset of predictors/features is used for creating the decision model. For each tree thus grown, a predictor is chosen to make a decision split at a particular node. This is usually done based on either the information gain/entropy or the Gini impurity that selects the best predictor for that particular node. This process is repeated at each node in a tree and subsequently multiple trees are trained. Final decisions are made based on averaging (for regression) or majority voting (for classification) of individual tree predictions.

The datasets for training and validating the Random Forests based classifier are obtained from ECG records present in the MIT-BIH Malignant Ventricular Ectopy Database (VFDB) and the American Heart Association Database (AHADB). The VFDB dataset contains rhythm-annotated 22 two-lead ECG recordings, each signal 30 minutes long and sampled at 250 Hz. The rhythms present in these records primarily include ventricular fibrillation, sustained ventricular tachycardia, ventricular utter, atrial fibrillation, asystole, high grade ventricular activity and noise. Similarly, the AHADB dataset consists of ECG recordings representing ventricular arrhythmias.

Prior to feature extraction for VT/VF detection, the signal is subject to ECG denoising and EM noise classification as previously described. Following that, the denoised signal is segmented into non-overlapping five-second epochs. From each five-second epoch, a total of seven features are derived. This feature derivation includes time-domain, frequency-domain and stationary wavelet transform (SWT) analysis. They are described below:

1. max_freq: Dominant frequency from Fourier analysis computed using Fast Fourier Transform (FFT). This feature is the primary frequency component (in Hz) present in the normalized FFT for the 5 s epoch. In the presence of sustained VT/VF, this will take a value in the range 2.5 Hz to 8 Hz, corresponding to approximately 150 bpm to 500 bpm which is the clinical heart rate range for sustained VT/VF episodes.
2. xft_ratio: Ratio of FFT ranges. This feature refers to the ratio between (i) FFT values corresponding to the range [2.5, 8] Hz and (ii) FFT values corresponding to the range [0, 20] Hz. This feature essentially indicates the extent to which clinically significant VT/VF frequency components dominate the frequency content of the five-second epoch.
3. ccf6: Pearson's Correlation Coefficient between the five-second epoch and its level-6 SWT detail coefficients, computed using Daubechies3 ('Db3') wavelet as the mother wavelet. At 360 Hz sampling frequency and using dyadic compression in the frequency domain, level 6 detail coefficients correspond to the frequency range [2.8, 5.6] Hz. Hence this feature measures how correlated the ECG epoch is with respect to the SWT level-6 coefficients. In the presence of VT/VF, this value is expected to be relatively large.

For one-dimensional vectors X and Y, this feature is computed as below (Johnson and Wichern, 2002):

$$Cov(X, Y) = \frac{\sum_{k=1}^{m}(X_k - \overline{X})(Y_k - \overline{Y})}{m-1} \quad (10)$$

$$R_{XY} = \frac{Cov(X, Y)}{\sqrt{Cov(X, X)Cov(Y, Y)}} \quad (11)$$

where m in Equation (10) is the number of samples in X (or Y), X refers to the five-second ECG epoch and Y refers to its SWT level-6 detail coefficients (both have the same length, m), $\overline{X}$ refers to the mean (i.e., average) of X, and $\overline{Y}$ refers to the mean of Y. It must be noted that the term Cov(X,X) in the denominator of Equation (11) is simply the variance of X. Similarly, Cov(Y, Y) refers to the variance of Y.

4. ccf7 Pearson's Correlation Coefficient between the five-second epoch and its level-7 SWT detail coefficients, computed using Daubechies3 ('Db3') wavelet as the mother wavelet. At 360 Hz sampling frequency and using dyadic compression in the frequency domain, level-7 detail coefficients correspond to the frequency range [1.4, 2.8] Hz. Hence this feature measures how correlated the ECG epoch is with respect to the SWT-level7 coefficients. In the presence of VT/VF, this value is expected to be relatively large. This feature is computed similar to that of ccf6, except that Y in Equations (10) and (11 refers to SWT level-7 detail coefficients.
5. ccf67: Pearson's Correlation Coefficient between the five-second epoch and the signal reconstructed using both SWT level-6 and level-7 coefficients. This feature is computed in a similar manner as the preceding two features, except that that Y in Equations (10) and (11) refers to the reconstructed signal.
6. Peak_corr: Peak auto-correlation value. This is the maximum amplitude of autocorrelation sequence computed for the five-second ECG epoch. The auto-correlation sequence is computed as follows:

$$Corr_X[l] = \sum_k X[k]X[k+l] \quad (12)$$

where l is the lth sample in $Corr_x$. The length of $Corr_x$ is $(2N_x-1)$ where $N_x$ is length of X i.e., the length of the ECG epoch. Since the ECG epoch is five seconds long, $N_x$ is equal to 1800 (at 360 Hz sampling frequency).

7. Auc_corr: This refers to the sum of the auto-correlation (computed using Equation (12)) coefficients. This is computed as follows:

$$sum\_corr = \sum_{k=1}^{2N_X-1} Corr_X[k] \quad (13)$$

In the presence of sustained VT/VF, both peak corr and auc_corr are expected to be relatively large. This can be attributed to the fact that the ECG is almost sinusoidal (owing to oscillatory waveforms) in the presence of sustained VT/VF and are therefore expected to be show a high degree of auto-correlation.

The seven features are input to a Random Forest classifier. This classifier was trained using the examples present in the training dataset. Hyperparameter tuning using Grid search was performed to identify the best parameters for the Random Forest model. The hyperparameter tuning search space for Random Forests included four primary hyperparameters as given in Table III (below). The last column in the table shows the best combination of parameters chosen i.e., the model trained with the combination of these particular parameter values was determined to achieve the best performance on the validation dataset. This model is labeled $VTVF_{model}$.

TABLE III

| Hyperparameter | Range of values | Best value |
| --- | --- | --- |
| Number of trees | [10, 15, 20, 25, . . . , 100] | 50 |
| Maximum tree depth | [5, 10, 15, . . . , 50, None] | 19 |
| Maximum features | [auto, 7] (auto: square root of number of features) | 7 |
| Class weight | ['balanced', None] | 'balanced' |

The Number of trees parameter refers to the number of trees in the Random Forests model. The Maximum tree depth parameter refers to the maximum depth of each tree. This is an important hyperparameter to select as deeper trees generally result in overfitting. The third hyperparameter, Maximum features refers to the number of features to be randomly selected for performing splits at each node. The last hyperparameter is the Class weight. This refers to the weight assigned to each class and plays a significant role in removing biases when dealing with imbalanced classes. By default, the 'balanced' option assigns weights inversely proportional to the class frequencies. It can be seen from Table III that the grid search selected the 'balanced' option for the Class weight parameter. This is because the training dataset is inherently imbalanced with an imbalance ratio of about 1:2.5.

The performance of $VTVF_{model}$ was evaluated on the training and validation datasets and the corresponding results are shown in Table IV. The training dataset consists of a total of 3124 VT/VF examples and 7958 Non-VT/VF examples. Similarly, the validation dataset consists of 2428 VT/VF examples and 8724 Non-VT/VF examples. ECG signals from both the leads were used for creating the datasets but they were used independent of each other so as to increase the data count for training and validation purposes.

TABLE IV

| Dataset | Se | PPV | FSc | Sp | Remarks |
|---|---|---|---|---|---|
| Training | 98.85 | 96.17 | 97.49 | 98.45 | Odd-numbered records from VFDB and AHADB |
| Validation | 97.90 | 95.77 | 96.89 | 98.80 | Even-numbered records from VFDB and AHADB |

The results are presented in terms of Sensitivity (Se), Positive predictive value (PPV), F-Score (FSc) and Specificity (Sp). The equations for these metrics are given in Equations (14) through (17).

$$Se = \frac{TP}{TP+FN} * 100 \quad (14)$$

$$PPV = \frac{TP}{TP+FP} * 100 \quad (15)$$

$$FSc = \frac{2*TP}{(2*TP)+FP+FN} * 100 \quad (16)$$

$$Sp = \frac{TN}{TN+FP} * 100 \quad (17)$$

where TP refers to the True Positives, i.e., correctly classified VT/VF examples; FP refers to False Positives i.e., Non-VT/VF examples misclassified as VT/VF; TN refers to True Negatives i.e., correctly classified Non-VT/VF examples; and FN refers to False Negatives, i.e., VT/VF examples that are misclassified as Non-VT/VF.

FIG. 13 and FIG. 14 show the confusion matrices depicting the performance of $VTVF_{model}$ on the training and validation datasets respectively. In these figures, the rows (upper case VT/VF and NON VT/VF) represent the true labels and the columns represent the predicted labels (lower case vt/vf and non vt/vf). From a two-dimensional mapping (not shown) of the seven PVC features, it can be seen that the PVC and non-PVC representations form (almost) disjoint class-specific clusters, thus indicating the usefulness of the seven features for distinguishing PVC beats from non-PVC beats.

Figure 15:
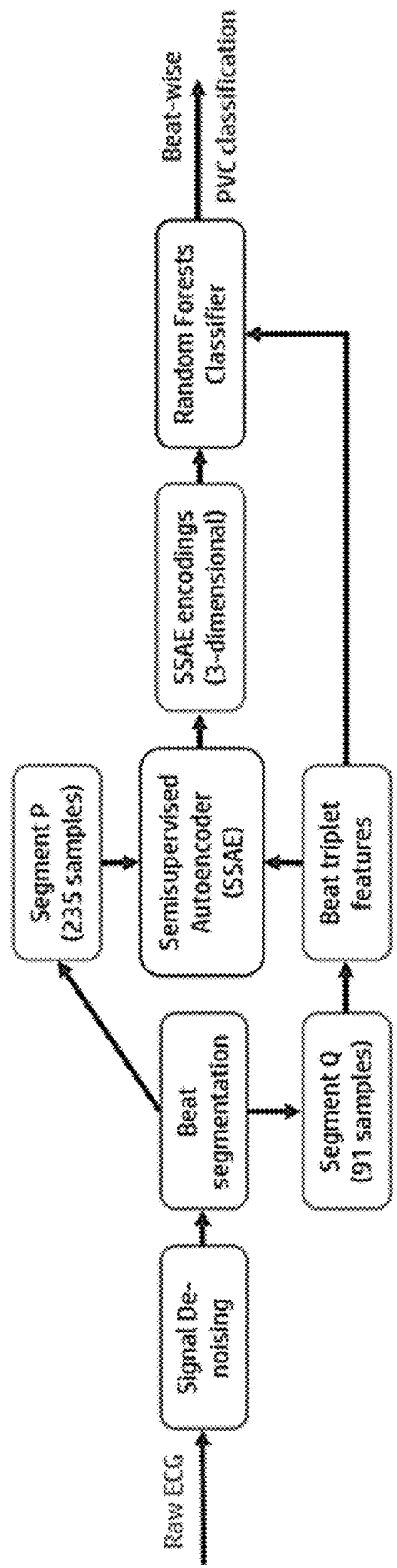
FIG. 15 shows a block diagram for an exemplary approach for ventricular entropy (PVC) classification in accordance with various embodiments of the present disclosure.

Next, for analysis of beat-dependent arrhythmias (e.g., step 206-209 of FIG. 2), techniques for accurate detection of premature ventricular complexes are featured. Accordingly, in various embodiments, a novel metadata-augmented deep-learning based method is presented to accurately detect PVCs from single lead ECG signals using a combination of a Semisupervised Autoencoder (SSAE) and Random Forest models. Raw ECG beat segments along with manual features derived from three consecutive beats are used to train the SSAE network so as to efficiently learn three-dimensional class-specific encodings (stage 1). The learnt encodings, along with the manually computed beat-triplet features, are then input to a Random Forests classifier for final PVC classification (stage 2). FIG. 15 shows the block diagram summarizing the approach.

In accordance with an exemplary implementation of this approach, the PVC classifier is trained, validated, and tested using ECG signals from records in the MIT-BIH Arrhythmia Database (MITDB) and the St. Petersburg INCART 12-lead Arrhythmia Database (INCARTDB), available from the Physionet database. The MITDB database consists of 48 two-lead ECG records, sampled at 360 Hz and 30 minutes in duration. The INCARTDB database consists of 75 twelve-lead ECG records, sampled at 257 Hz and 30 min in duration. AAMI (ANSI/AAMI EC57:2012, 2012) standards are followed for beat labelling. Forty-four records from MITDB are split into training (MITDB-DS1) and validation (MITDB-DS2) datasets). The remaining four records have been omitted from analysis owing to presence of paced beats as per AAMI recommendations. The INCARTDB records form the test dataset. In an exemplary implementation of the present disclosure, Fusion and Supraventricular beats are considered as non-PVC beats while unclassified (Q) and aberrated beats are omitted from analysis. ECG signals from leads MLII and lead-II are used for MITDB and INCARTDB databases respectively.

As previously discussed, acquired ECG signals undergo denoising techniques (e.g., baseline wander removal and high frequency noise suppression). Following denoising, electrode motion (EM) noise classification is performed. Subsequently beat detection is performed and these beat locations are then used to create the features required for accurate PVC classification.

For feature extraction, at least three consecutive beats are used for performing PVC classification, owing to the manner in which the features are computed. For training, validating, and testing the models used in PVC classification, R-peak locations are used from the corresponding manual annotations available at Physionet for records in each dataset. For each R-peak, two ECG beat segments, namely P and Q, are derived from the denoised ECG signal. Beat segment P is obtained using a window of 250 ms prior to the R-peak location and 400 ms afterward (a total of 235 samples at 360 Hz sampling frequency). Similarly, beat segment Q is obtained using a window of 125 ms prior to the R-peak location and 125 ms afterward (91 samples). These two segments are used to create inputs for training a semisupervised autoencoder.

As it can be observed, the autoencoder has two input layers. The first set of input is simply the 235 samples of beat segment P. The second set of inputs to the autoencoder comprises four features computed from three consecutive R-peaks ($r_i$, $r_{i-1}$, $r_{i-2}$):
  (i) RR-interval in terms of heart rate (HR). RR-interval is simply the duration between the two consecutive R-peaks given by Equation (48). For each R-peak $r_i$; this feature is computed as follows:

$$rr_i = r_i - r_{i-1} \quad (18)$$

$$HR_i = (Fs*60)/rr_i \quad (19)$$

where Fs is the sampling frequency i.e., 360 Hz.

(ii) Successive Difference of RR-intervals in percentage (%) (SDRR). This is the percentage change in duration between two consecutive RR intervals:

$$SDRR_i = \frac{rr_i - rr_{i-1}}{rr_{i-1}} * 100 \quad (20)$$

(iii) Correlation Coefficient ($R_{i,i-1}$). This feature is computed using beat segments $Q_i$ and $Q_{i-1}$ that correspond to R-peaks $r_i$ and $r_{i-1}$. For one-dimensional vectors $Q_i$ and Qi−1; this feature is computed as below (Johnson and Wichern, 2002):

$$Cov(X, Y) = \frac{\sum_{k=1}^{m}(X_k - \overline{X})(Y_k - \overline{Y})}{m - 1} \quad (21)$$

$$R_{i,i-1} = \frac{Cov(Q_i, Q_{i-1})}{\sqrt{Cov(Q_i, Q_i)Cov(Q_{i-1}, Q_{i-1})}} \quad (22)$$

where m in Equation 21 is the number of samples in $Q_i$ (or $Q_{i-1}$).

(iv) The last feature is the Skewness of Cross-correlation (SCC). As the name implies, this is skewness (Zwillinger and S. Kokoska, 2000) of the cross-correlation sequence computed between segments $Q_i$ and $Q_{i-1}$. Cross-correlation ($Corr_{X,Y}$) of two sequences, X and Y, is computed as:

$$Corr_{X,Y}[l] = \sum_k X[k]Y[t+l] \quad (23)$$

where l is the lth sample in $Corr_{X,Y}$. The length of $Corr_{X,Y}$ is $m_X+m_Y-1$, where $m_X$ and $m_Y$ are the number of samples in X and Y respectively. $SCC_i$ is then computed as follows:

$$\mu_3(X) = \frac{1}{M}\sum_{k=1}^{M}(X_k - \overline{X})^3 \quad (24)$$

$$Skew(X) = \frac{\mu_3(X)}{(Cov(X, X))^{3/2}} \quad (25)$$

$$SCC_i = Skew(Corr_{Q_i,Q_{i-1}}) \quad (26)$$

where M is the number of samples in X, $\mu_3(X)$ is the third central moment of X (Zwillinger and S. Kokoska, 2000). Additionally, the sequence $Corr_{Qi,Qi-1}$ is scaled in the range [−1,1] before using it in Equation (26).

Figure 16:
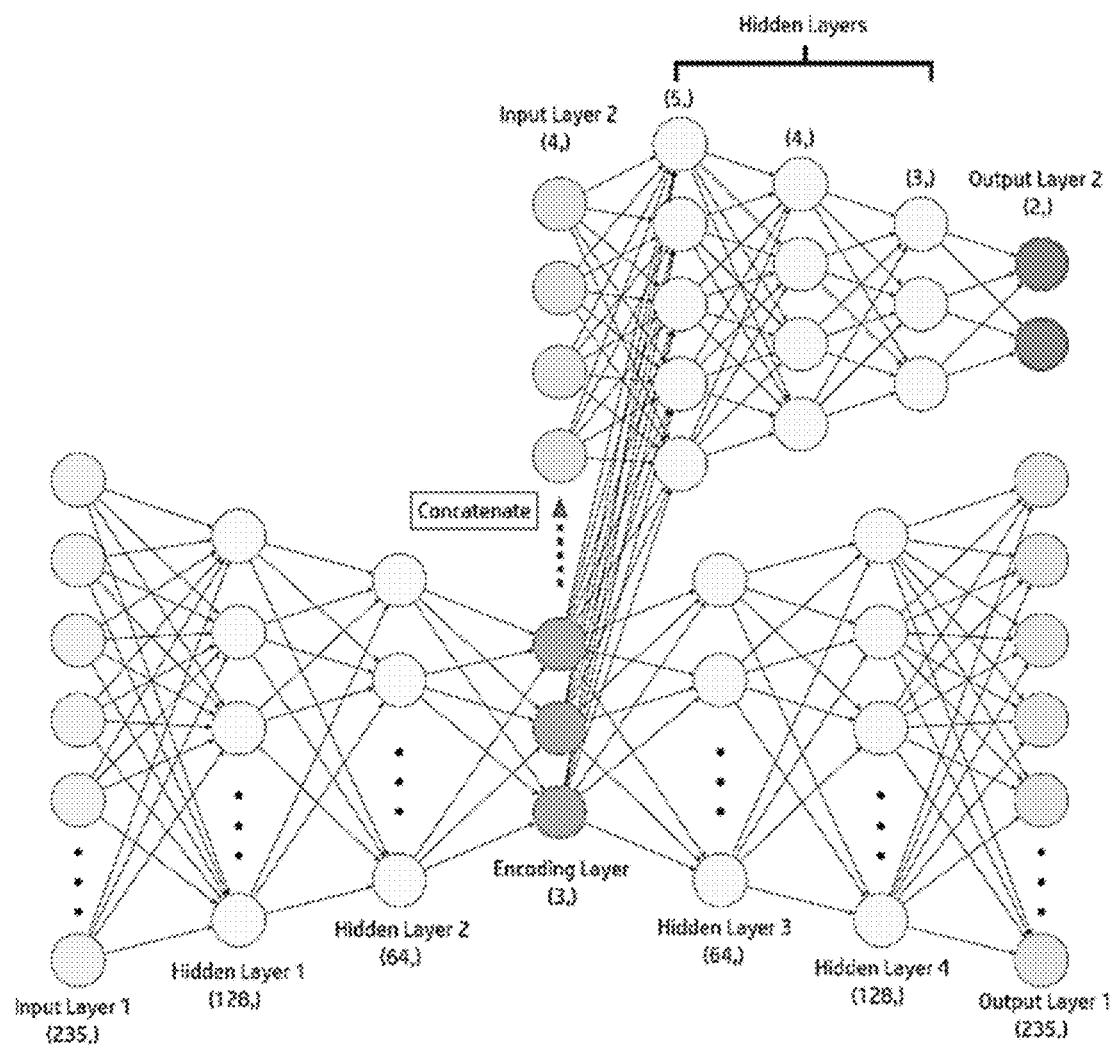
FIG. 16 shows the architecture of an exemplary semisupervised autoencoder network in accordance with various embodiments of the present disclosure.

In various embodiments, a neural-network based semisupervised autoencoder is implemented to efficiently learn three-dimensional encodings of individual ECG beat morphologies that will be used as features for final PVC classification. The network is semisupervised in that the architecture consists of an autoencoder component (unsupervised learning) and a binary classifier neural network (supervised learning) embedded together. Unlike traditional autoencoders, the architecture here actually uses manually computed features (Input Layer 2 in FIG. 16) along with raw ECG data (Input Layer 1 in FIG. 16). This helps the network to not only learn low-dimensional encodings of beat morphologies but also ensures that these encodings are suitable to be used as features for distinguishing PVC from non-PVC beats. It should be noted that the binary classifier component used here is for generating class-specific encodings only and not for final PVC classification. The overall architecture of the SSAE network is shown in FIG. 16. The input to Input Layer 1 is the raw ECG samples of segment P (scaled in the range [−1,1]). The input to Input Layer 2 consists of the beat-triplet features. Input Layer 2 is concatenated with the output of Encoding Layer to form the overall input to the binary classifier component (see FIG. 16). The target data for Output Layer 1 (autoencoder's decoder output) is identical to the input of Input Layer 1. Output Layer 2 is the binary classifier component's output and its target data corresponds to the output class (label) of each beat i.e., PVC or non-PVC. Ideally, the output of this layer should be $[0; 1]^T$ for PVC beats and $[1; 0]^T$ otherwise.

The records in the MITDB-DS1 dataset are used for training the SSAE network. This hybrid network is trained end-to-end using backpropagation ReLU (Rectified Linear Units) activation function is used for the hidden layers while "tanh" and "softmax" activations are applied to Output Layer 1 and Output Layer 2 respectively. Layer weights that gave the best performance, in terms of F-score, on the validation dataset (MITDB-DS2) are selected and the SSAE network with these layer weights is labeled SSAEbest. The three-dimensional encodings (output of Encoding Layer) from the SSAEbest model constitute the SSAE-derived features.

For PVC classification, the SSAE-derived features along with beat-triplet features, all computed from records in MITDB-DS1 dataset, are used for training a binary Random Forests model for detecting PVC beats. Hyper-parameter tuning using Grid Search is employed for selecting the best Random Forests model for PVC classification. The hyper-parameter tuning search space for Random Forests included four primary parameters as given in Table V (below).

TABLE V

| Hyperparameter | Range of values | Best value |
| --- | --- | --- |
| Number of trees | [10, 11, 12, . . . , 250] | 162 |
| Maximum tree depth | [5, 10, 15, . . . , 50, None] | None |
| Maximum features | [auto, 7] (auto: square root of number of features) | auto |
| Class weight | ['balanced', None] | 'balanced' |

The occurrence of PVCs in certain specific patterns gives rise to different ventricular arrhythmias. Since these patterns are clearly defined in medical literature, simple logical analysis that searches for these patterns is implemented to detect the presence of these arrhythmias. It must be remembered that this logical analysis step is based on beat label information obtained in the PVC classification stage and hence the detection accuracy for these arrhythmias inherently depends on the accuracy of PVC detection. These arrhythmias and the logic required to detect them are briefly discussed below.

Ventricular Bigeminy (VBI) refers to the occurrence of alternating PVC and non-PVC beats. To confirm ventricular bigeminy, presence of at least three consecutive pairs of Non-PVC/PVC beats is required. If PVC beats are denoted as V and non-PVC beats are denoted as N, then an exemplary ventricular arrhythmia analysis algorithm and related processes search for the pattern [NVNVNV . . . ]. Hence at least six beats are required to detect presence of VBI episodes. The occurrence of two consecutive N beats marks the end of a ventricular bigeminy episode. To detect another episode, the algorithm once again searches for the sequence [NVNVNV . . . ] in the remaining beats. Once the sequence is found, it marks the onset of another VBI episode and continues scanning until it encounters two consecutive N beats which marks the offset of this new episode. This process is repeated for all the remaining beats in the input ECG signal.

Ventricular Trigeminy (VTRI) refers to the occurrence of a PVC beat after every two consecutive non-PVC beats. To confirm ventricular trigeminy, presence of at least three consecutive triplets of the form [NNV] is required. To detect a Ventricular Trigeminy episode, an exemplary ventricular arrhythmia analysis algorithm and related processes search for the pattern [NNVNNVNNV . . . ]. Hence at least nine beats are required for detection of VTRI episodes. The occurrence of any beat-triplet other than [NNV] beat-triplet marks the end of a ventricular trigeminy episode. To detect another episode, the algorithm once again searches for the sequence [NNVNNVNNV . . . ] in the remaining beats. Once the sequence is found, it marks the onset of another VTRI episode and continues scanning until it encounters a beat-triplet other than [NNV] which marks the offset of this new episode. This process is repeated for all the remaining beats in the input ECG signal.

Ventricular Quadrigeminy (VQUAD) refers to the occurrence of a PVC beat after every three consecutive non-PVC beats. To confirm ventricular quadrigeminy, presence of at least three consecutive quadruplets of the form [NNNV] is required. To detect a ventricular trigeminy episode, an exemplary ventricular arrhythmia analysis algorithm and related processes search for the pattern [NNNVNNNVNNNV . . . ]. Hence at least twelve beats are required for detection of VQUAD episodes. The occurrence of any beat-quadruplet other than [NNNV] beat-triplet marks the end of a ventricular quadrigeminy episode. To detect another episode, the algorithm once again searches for the sequence [NNNVNNNVNNNV . . . ] in the remaining beats. Once the sequence is found, it marks the onset of another VQUAD episode and continues scanning until it encounters a beat-quadruplet other than [NNNV] which marks the offset of this new episode. This process is repeated for all the remaining beats in the input ECG signal.

Ventricular runs refer to occurrence of three or more consecutive PVCs at heart rates greater than 100 bpm. At heart rates greater than 120 bpm, these rhythms are also known as Short Ventricular Tachycardia episodes. In fact, when ventricular runs persist for a duration greater than 30 s at heart rates exceeding 150 bpm, it leads to sustained VT episodes. To detect ventricular runs, an exemplary ventricular arrhythmia analysis algorithm and related processes search for groups of three or more consecutive PVC beats. For every group of three or more consecutive PVC beats, the mean heart rate is computed as follows:

$$RR_{group} = \frac{1}{n-1}\sum_{k=1}^{n-1} rr_k \quad (27)$$

$$HR_{group} = \frac{Fs*60}{RR_{group}} \quad (28)$$

where n is the number of PVCs in the beat group, $rr_k$ is the kth RR-interval in the group, computed using Equation (18), and Fs is the sampling frequency.

Ventricular couplets or pairs refer to occurrence of exactly two consecutive PVCs at heart rates greater than 100 bpm. To detect ventricular couplets, an exemplary ventricular arrhythmia analysis algorithm and related processes search for the presence of [VV] pattern in the beats and each such pair is marked as a ventricular couplet episode.

The performance of an exemplary ventricular arrhythmia analysis algorithm and related processes in detecting the occurrence of PVCs in certain specific patterns were evaluated on the MITDB and INCARTDB databases. The MITDB-DS1 dataset has 3680 PVC and 47055 non-PVC examples. Similarly, the MITDB-DS2 dataset consists of 3218 PVC and 46370 non-PVC examples while the INCARTDB dataset consists of 19990 PVC and 155684 non-PVC examples. This information is summarized in Table VI (below).

TABLE VI

| Type | Dataset | PVC | Non PVC | Total |
| --- | --- | --- | --- | --- |
| Training | MITDB-DS1 | 3680 | 47055 | 50735 |
| Validation | MITDB-DS2 | 3218 | 46370 | 49588 |
| Test | INCARTDB | 19990 | 155684 | 175674 |

Table VII (below) shows the performance scores of the exemplary ventricular arrhythmia analysis algorithm and related processes in detecting the occurrence of PVCs. The results are provided in terms of Sensitivity (Se), positive predictive value (PPV) and F-Score (FSc). These metrics are computed using Equations (14) through (16). It can be seen that the exemplary algorithm achieves a sensitivity of 100.00%, PPV of 98.55% and FSc of 99.27% on the training (MITDB-DS1) dataset. Similarly, it achieves a sensitivity of 92.67%, PPV of 95.88% and FSc of 94.10% on the validation (MITDB-DS2) dataset while achieving a sensitivity of 88.08%, PPV of 94.76% and FSc of 91.30% on the test (INCARTDB) dataset.

TABLE VII

| Dataset | Se | PPV | FSc |
| --- | --- | --- | --- |
| MITDB-DS1 (Training dataset) | 100.00% | 98.55% | 99.27% |
| MITDB-DS2 (Validation dataset) | 92.67% | 95.58% | 94.10% |
| MITDB (Overall) | 96.58% | 97.20% | 96.89% |
| INCARTDB (Test dataset) | 88.08% | 94.76% | 91.30% |

Since the SSAE network also has a binary classifier component, initial PVC classification performance using the SSAE network was evaluated. The corresponding results are shown in Table VIII (below).

TABLE VIII

| Dataset | Se | PPV | FSc |
| --- | --- | --- | --- |
| MITDB-DS1 (Training dataset) | 96.37% | 85.93% | 91.03% |
| MITDB-DS2 (Validation dataset) | 96.02% | 83.33% | 91.07% |
| MITDB (Overall) | 96.42% | 84.70% | 90.18% |
| INCARTDB (Test dataset) | 92.96% | 89.90% | 91.07% |

It can be seen from Table VIII that using the SSAE network alone results in decreased values of precision (PPV) and subsequently decreased F-Score (FSc) values compared to the final results in Table VII. This was the primary motivation behind using the additional Random Forests model for final PVC classification. The accuracy statistics in Table VII and Table VIII reflect the performance of the PVC classification on features derived using manual R-peak annotations for the MITDB and INCARTDB records. Since the present disclosure is focused on developing a fully automated arrhythmia analysis system, it is imperative that the above described algorithm performs well on R-peaks obtained using an automated R-peak detection approach. In that regard, Table IX (below) shows the performance of the PVC classification algorithm and related processes using R-peaks that were determined by the beat detection algorithm. The results in this table are shown for all the records in each database.

TABLE IX

| Dataset | Se | PPV | FSc |
| --- | --- | --- | --- |
| MITDB | 93.17% | 94.41% | 93.79% |
| INCARTDB | 88.55% | 89.06% | 88.80% |

From a two-dimensional mapping (not shown) of the seven PVC features, it can be seen that the PVC and non-PVC representations form (almost) disjoint class-specific clusters thus indicating the usefulness of the seven features for distinguishing PVC beats from non-PVC beats. Next, FIG. 17, FIG. 18, and FIG. 19 show the confusion matrices depicting the performance of the PVC classification model on the training, validation, and test datasets respectively. In these figures, the rows (upper case PVC and NON PVC) represent the true labels and the columns represent the predicted labels (lower case pvc and non pvc).

Figure 20:
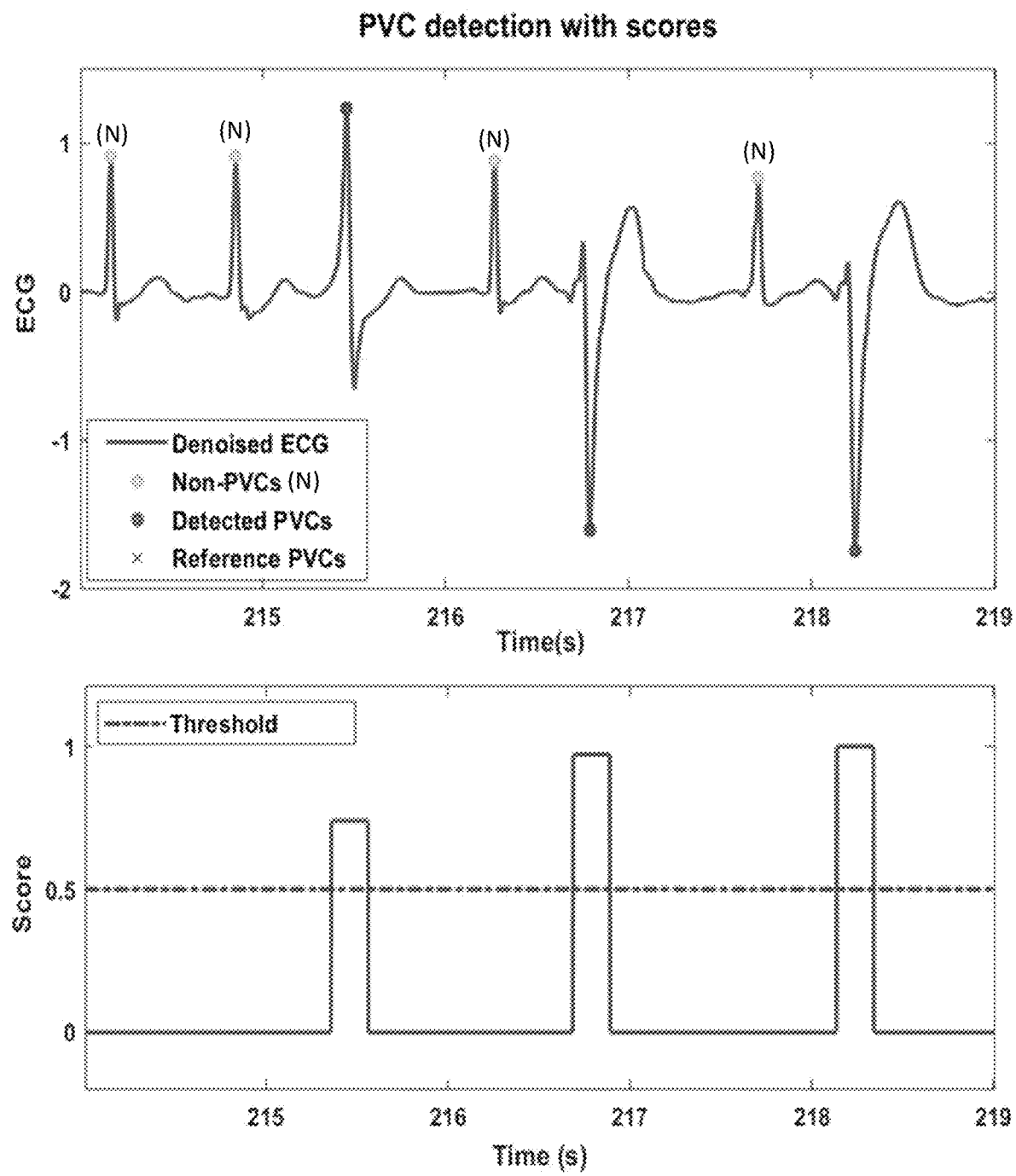
FIG. 20 demonstrates the detection of multi-form PVCs in a 5-second ECG segment for an exemplary arrhythmia analysis algorithm and related processes in detecting the occurrence of PVCs in accordance with various embodiments of the present disclosure FIG. 21 and FIG. 22 provide tables showing the comparison statistics with an exemplary arrhythmia analysis algorithm and related processes in detecting the occurrence of PVCs and state-of-the-art methods for MITDB-DS2 and INCARTDB databases respectively.

Correspondingly, FIG. 20 shows an example of PVC detection in a 5-second ECG segment. In the figure, the top plot shows the denoised ECG with the exemplary arrhythmia analysis algorithm's PVC and non-PVC classifications along with reference PVC labels. The bottom plot shows the classification scores of the Random Forests model for each beat. Scores above the 0.5 threshold correspond to PVC beats. It can be seen that the PVCs in this example have varied morphologies (the first one has positive QRS polarity while the remaining two PVCs exhibit negative QRS polarity), and the algorithm detects all of them. This demonstrates the algorithm's ability to robustly detect multiform PVCs.

We compared the performance of an exemplary arrhythmia analysis algorithm and related processes in detecting the occurrence of PVCs with other state-of-the-art techniques in literature for PVC classification. FIG. 21 and FIG. 22 show tables with comparison statistics for MITDB-DS2 and INCARTDB databases respectively. It must be noted that for the purpose of comparisons, results provided in Table VII are used as the other works report their results based on manual R-peak annotations. It can be seen that the exemplary PVC classification algorithm performs comparably or better than the other methods. It has to be noted the algorithms of (Oster et al., 2015) are not automatic (they involve expert assistance) while the authors of (Llamedo and Martinez, 2012) use multi-lead (leads II and V1) rather than single-lead ECG information from the INCARTDB records in their approach. Also, the authors of (de Chazal and Reilly, 2006) and (Kiranyaz et al., 2016) include a subset of beats from the MITDB-DS2 dataset as part of their training data (see footnotes for tables represented in FIGS. 21 and 22).

In brief, under step 204 and steps 206-209 of FIG. 2, processes for automated detection of ventricular arrhythmias are performed. For step 204, beat-independent arrhythmias such as ventricular fibrillation and sustained ventricular tachycardia can be detected using time-domain and feature-domain features along with SWT analysis. In various embodiments, these features are input to a Random Forests classifier to achieve accurate VT/VF detection performance on VFDB and AHADB ECG records. Additionally, under steps 206-209, novel techniques for the automatic detection of beat-dependent arrhythmias based on PVC beats can also be performed. In various embodiments, a combination of semisupervised autoencoders and random forests is used for achieving accurate PVC detection results, which demonstrate superior performance over current-state-of-the art techniques that utilize only single-lead ECG data and that do not require expert assistance. Upon completion of the steps involving analysis and detection of ventricular arrhythmias, steps that focus on detecting supraventricular arrhythmias can commence.

Supraventricular arrhythmias refer to cardiac rhythms that originate in the cardiac cells above the ventricles. This includes the atrio-ventricular (AV) node, atria and the Sino-Atrial (SA) node. The electrical impulses may be abnormally conducted from any of these sites. When the atria initiate cardiac cycles by abnormally_ring electrical impulses, it results in occurrence of Premature Atrial Complexes (PACs). On the other hand, when these ectopic beats are initiated in the AV node, this results in occurrence of Premature Junctional Complexes (PJCs). Although the SA node is the heart's natural pacemaker, still there may be irregularities associated with its impulse discharge. For example, the SA node may fire slower than usual due to conduction blocks which could result in Sinus Bradycardia. Similarly, abnormally rapid electrical discharges from the SA node could result in presence of Sinus Tachycardia. In the present disclosure, no distinction is made between PACs and PJCs in terms of detection and are together termed Supraventricular Beats (SVEBs). The supraventricular arrhythmias discussed in the present disclosure include (1) Atrial Fibrillation, (2) Supraventricular Ectopic Beats, (3) Supraventricular Bigeminy, (4) Supraventricular Trigeminy, (5) Supraventricular Quadrigeminy, (6) Supraventricular Couplets, (7) Supraventricular Runs, and (8) Sinus Bradycardia.

Although atrial fibrillation (AF) is theoretically a sequence of supraventricular ectopic beats and hence a supraventricular arrhythmia, in accordance with various embodiments, AF is detected using fixed-length ECG segments (60 epochs) whereas SVEBs and remaining arrhythmias are detected on a beat-by-beat basis. Hence, in various embodiments, AF detection is carried out first followed by detection of SVEBs and other arrhythmias.

Automated methods for classification of AF episodes generally rely on the information extracted from electrocardiogram (ECG) signals. The absence of periodically occurring P-waves or presence of fibrillatory f-waves in ECG (seen as undulations of the isoelectric baseline) coupled with irregular heart rate fluctuations are primary indicators of AF. Despite the significant progress made in understanding the factors contributing to occurrence of atrial fibrillation episodes, development of automated techniques to detect AF episodes remains far from achieving satisfactory results due to several factors. First, there are several other arrhythmias that typically mimic AF in terms of their manifestation on the ECG as well as possessing similarities in terms of spectral content, extent of heart rate variability, etc. Secondly, the presence of external noise, especially owing to electrode/patient movements, hinders the performance of AF classifiers severely, giving rise to increased misclassification rates, and this gains further significance in the context of today's wearable sensors. These aforementioned factors necessitate the need to develop an AF classifier that is highly robust to noise while being capable of accurately identifying AF rhythms, especially in the presence of other similar arrhythmias.

Although deep learning techniques offer an attractive alternative to hand-computed feature extraction, limited availability of labeled AF datasets acts as a major bottleneck for training robust deep learning models for AF classification. In comparison, various embodiments of an exemplary approach towards AF classification of the present disclosure is characterized primarily by implementing a combination of Markov models and Random Forests classifiers to perform noise assessment and RR-interval based AF classification. The inconsistency in the detection of P-waves and delineation of fibrillatory f-waves from noisy ECG recordings contributed to omitting atrial activity analysis in the exemplary approach described in the present disclosure. The use of an eight-state Markov matrix for AF classification, complemented by Random-Forest based feature-learning ensures that an exemplary AF detection algorithm can effectively distinguish AF from other arrhythmias. The use of Markov models offers the advantage that sequential pattern changes in heart rates can be effectively captured, thus aiding in better distinction between AF and other arrhythmias with prominent heart rate variations. These Markov probabilities, along with other statistical parameters that help quantify randomness in RR-interval transitions, are input to a Random Forests based AF classifier for initial AF classification.

In an exemplary implementation, the Random Forests model used for AF classification was trained, validated, and tested using features derived from datasets available in the Physionet database. For training the AF classification model, ECG records from the MIT-BIH Atrial Fibrillation Database (AFDB) (Moody, 1983) were used. On the other hand, ECG records from the MIT-BIH Arrhythmia Database (MITDB) were used to form the test dataset.

For initial AF classification, the R-peak, indices i.e., beat locations, labeled $r_{pk}$, are used to create RR-interval analysis based features vectors to detect AF presence. The derivation of these features is described subsequently.

First, the input signal is segmented into 60 s epochs with a 30 s sliding window. For each 60 s epoch, the corresponding R-peaks stored in $r_{pk}$ are used to create feature vectors using the steps described below:

1. The RR-interval time-series is computed as follows:

$$rr_{n-1} = r_n - r_{n-1}, 2 \leq n \leq N \quad (29)$$

where N is the total number of R-peaks in the epoch and rn is index of nth R-peak in the epoch –rr is the RR-interval series. It must be noted that R-peaks classified as PVCs are excluded from this computation.

2. The successive difference of RR-intervals (ΔRR) in percentage values, $rr_{per}$, is next calculated as follows:

$$rr_{per(n-1)} = 100 * \frac{(rr_n - rr_{n-1})}{rr_{n-1}}, \quad (30)$$

$$2 \leq n \leq N - 1$$

3. The $rr_{per}$ series is discretized into 8 different states as per Table X (below). This discretized series is labeled as $rr_d$ with the $rr_{per}$ boundaries for each state having been determined empirically.

TABLE X

| ΔRR values ($rr_{per}$) | State ($rr_d$) |
|---|---|
| (−∞, −50) | 1 |
| (−50, −30) | 2 |
| (−30, −15) | 3 |
| (−15, +15) | 4 |
| (+15, +45) | 5 |
| (+45, +75) | 6 |
| (+75, +100) | 7 |
| (+100, +∞) | 8 |

An 8-by-8 discrete-state Markov matrix B for the $rr_d$ state sequence is computed as follows:

$$\forall i, j \in [1, \ldots, 8]$$

$$B_{ij} = P(next_{state} = j \mid current_{state} = i) \quad (31)$$

$$\sum_{j=1}^{8} B_{ij} = 1, \quad 1 \leq i \leq 8 \quad (32)$$

In the presence of AF, the Markov matrix B is more densely populated than in the presence of other arrhythmia with similar magnitude of heart rate variation, such as ventricular bigeminy/trigeminy/quadrigeminy, etc. This can be attributed to the fact that the variations between successive RR-interval values are random in AF episodes and do not follow any specific pattern. On the other hand, the variations in heart rates for ventricular bigeminy/trigeminy, etc. is more regular and deterministic in which case the matrix B is sparsely populated.

Figure 23:
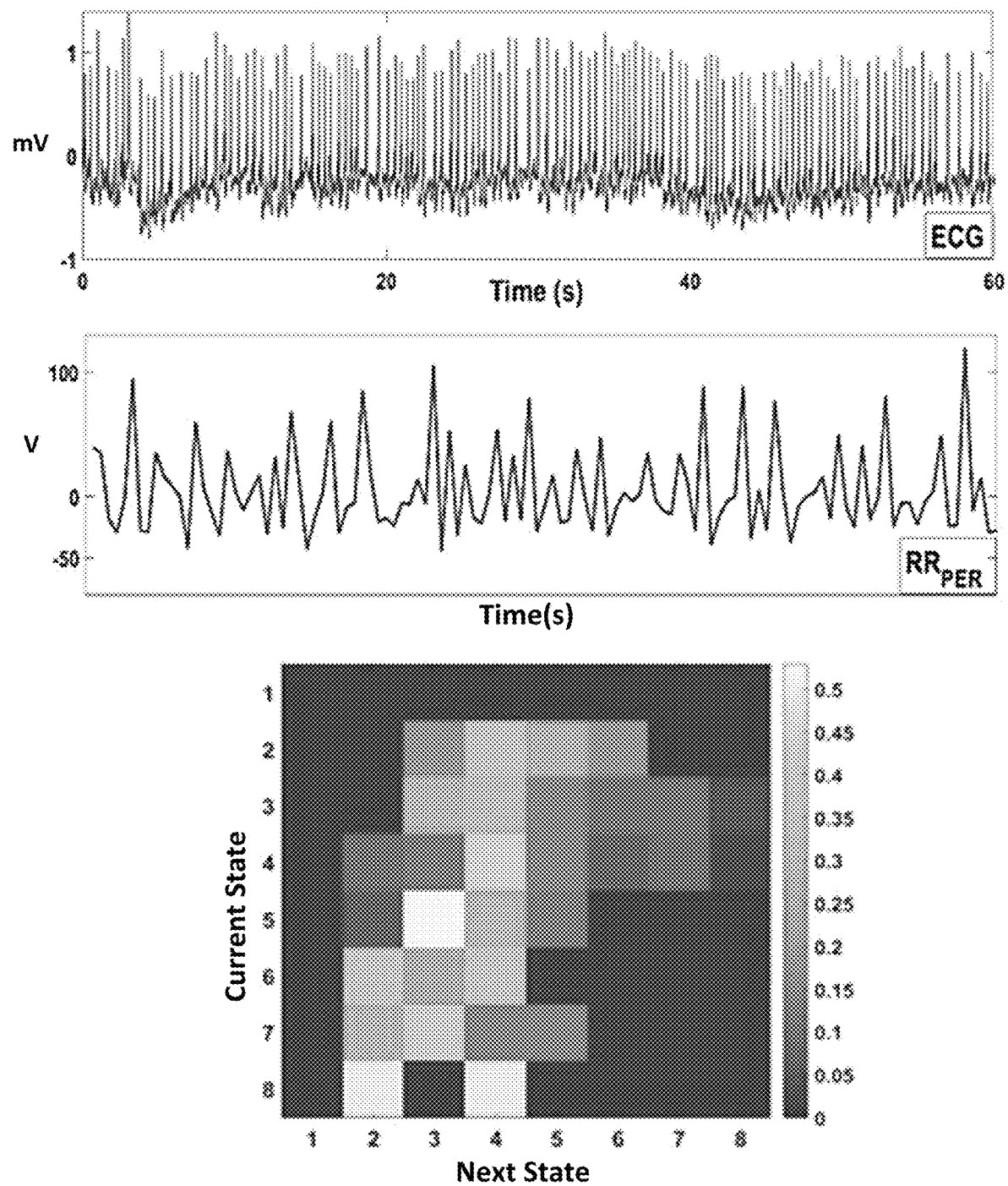
FIG. 23 demonstrates an ECG segment positively dominated by atrial fibrillation rhythms and a corresponding Markov matrix.
Figure 24:
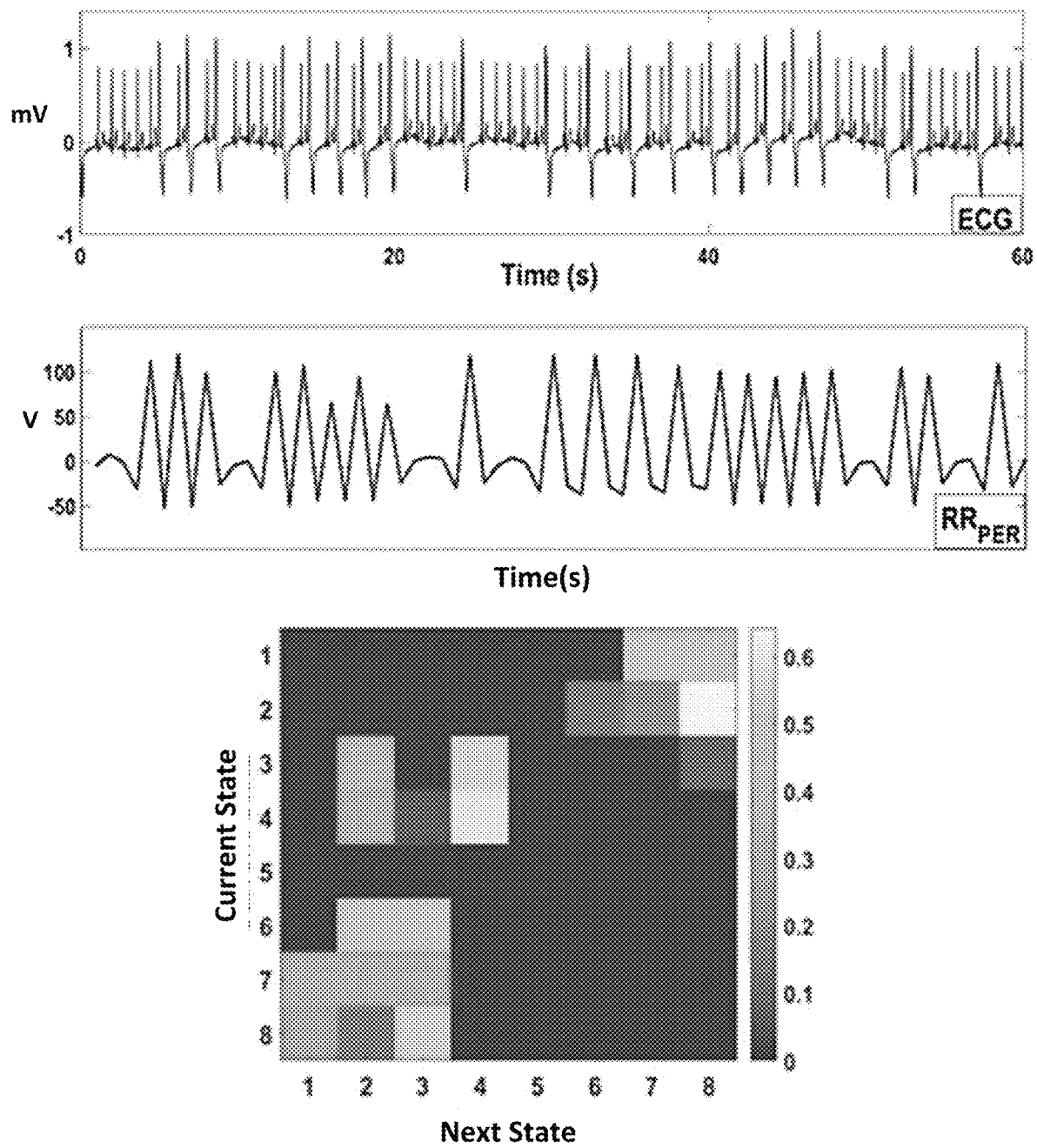
FIG. 24 demonstrates an ECG segment negatively dominated by atrial fibrillation rhythms and a corresponding Markov matrix.

FIG. 23 shows an ECG segment completely dominated by AF rhythm. The corresponding Markov matrix (bottom plot) has values that are spread about the center of the matrix in a largely random fashion, indicating lack of discernible patterns in the heart rate variations. On the other hand, FIG. 24 represents a 60 s long ECG epoch containing episodes of ventricular trigeminy, ventricular bigeminy and normal sinus rhythm coupled with a few ectopic beats. Although there is significant amount of heart rate variation here as well, evidenced by the $rr_{per}$ series (in the middle subplot), the corresponding Markov matrix in the bottom plot looks vastly different. Here, most of the transition probability values are concentrated near the left-bottom and top-right corners of the matrix indicating the presence of specific sequential patterns in the RR-interval series. The elements of this 8-by-8 discrete-state Markov matrix form the first 64 features for AF classification.

The other feature obtained from the Markov matrix B is the total number of zero-valued elements present in it. This quantity reflects a measure of sparsity of the Markov matrix and in the presence of AF, this value is expected to be remain minimal.

Apart from the features derived from the Markov matrix as described above, eight other RR-interval based features are also computed to help distinguish AF from other similar rhythms effectively. They are as follows:

1. Entropy of the $rr_d$ state sequence, which indicates the extent of randomness in the RR-interval transitions. This entropy measure is computed using natural logarithm as follows:

$$e_{ss} = (-1) * \sum_{k=1}^{8} [p(s_k) * \log_e p(s_k)] \quad (33)$$

where ess is entropy of the $rr_d$ state sequence and $p(s_k)$ is the probability of occurrence of kth state in the $rr_d$ state sequence.

2. The p-value of Kolmogorov-Smirnov test (Stephens, 1974) for normality, applied to the $rr_{per}$ series. The null hypothesis (H=0) is that the $rr_{per}$ series follows a normal distribution which is the case for AF. The test is conducted at significance level of 5% and the p-values when the AF is present is generally much greater than 0.05.

3. Coefficient of variation of the RR-interval series, computed as per the equation below:

$$coeff_{var} = \frac{\sigma_{RR}}{\mu_{RR}} * 100 \quad (34)$$

where, $\sigma_{RR}$ is the standard deviation of RR-interval series without the smallest and largest intervals. Similarly, $\mu_{RR}$ is the mean of the RR series without the smallest and largest intervals.

4. The remaining two features are based on heart-rate quartiles derived from the RR-interval series. They include the difference between second and first quartiles and the difference between third and second quartiles.

5. All the above features together form a 70-element feature vector for each epoch. Subsequently, an [M×70] matrix is created where M is the total number of 60 s epochs in the ECG signal (with 30 s slide interval). This feature matrix is fed as input to a Random Forests based classifier that classifies each row of the feature matrix (i.e., each epoch) as either exhibiting AF presence or not.

In various embodiments, the 70 features may then be used for training a binary Random Forests classifier for detecting PVC beats. Five-fold cross validation is performed and hyperparameter tuning using Grid Search is employed for selecting the best model parameters for AF classification. The hyperparameter tuning search space for Random Forests included four primary parameters as given in Table XI (below).

TABLE 5.2

| Hyperparameter | Range of values | Best value |
| --- | --- | --- |
| Number of trees | [10, 11, 12, . . . , 250] | 116 |
| Maximum tree depth | [5, 10, 15, . . . , 50, None] | None |

TABLE 5.2-continued

| Hyperparameter | Range of values | Best value |
| --- | --- | --- |
| Maximum features | [auto, 5, 10, 15, . . . , 70] (auto: square root of number of features) | 15 |
| Class weight | ['balanced', None] | 'None' |

The performance of an exemplary arrhythmia analysis algorithm and related processes in detecting the presence of atrial fibrillation (AF) was evaluated on the MIT-BIH Atrial Fibrillation Database (AFDB) and the MIT-BIH Arrhythmia Database (MITDB). The AFDB database has 23 two-lead ECG records, each sampled at 250 Hz and having a duration of approximately 10 hours (except record 06453 which has a duration of approximately 9 hours). The MITDB database contains 48 two-lead ECG records, each sampled at 360 Hz and 30 min long. Out of these 48 records, eight records have substantial AF presence. Signals from lead ECGI for AFDB and lead MLII for MITDB databases are used respectively. Atrial Flutter and Junctional arrhythmias in the AFDB records are grouped as non-AF in this evaluation. Since 60 s epochs are used in an exemplary implementation of an AF detection algorithm here, it would be unfair to compare the results with beat-to-beat annotations. Hence, instead the true beat-to-beat annotations are converted into 60 s-epoch annotations. A 60 s epoch was annotated as having AF only if at least 50% of the beats in that epoch were originally annotated as AF beats. Using this approach, 135 AF epochs and 1304 non-AF epochs were obtained for the MITDB database. Similarly, 5528 AF epochs and 8226 non-AF epochs were obtained for the AFDB database.

The cross-validation results for all combinations in the Grid Search are presented in Table XII. From these, the best combination of parameters, shown in last column of Table XI, was chosen and an RF model with these parameters was retrained on the entire AFDB training dataset and labeled $AF_{model}$. The evaluation results of $AF_{model}$ are summarized in terms of sensitivity (Se), Specificity (Sp), positive predictive value and F-score (FSc) metrics in Table XIII. The equations for computing the above three evaluation metrics are as follows:

$$Se = \frac{TP}{TP + FN} * 100 \quad (35)$$

$$Se = \frac{TN}{TN + FP} * 100 \quad (36)$$

$$PPV = \frac{TP}{TP + FP} * 100 \quad (37)$$

$$FSc = \frac{2 * TP}{(2 * TP) + FP + FN} * 100 \quad (38)$$

where Se refers to sensitivity, Sp refers to specificity, and FSc refers to FScore for AF detection. TP refers to the number of true positives, i.e., correctly detected AF segments; FN refers to number of false negatives, i.e., AF epochs misclassified as non-AF; TN refers to the number of true negatives, i.e., correctly detected non-AF segments; and FP refers to the number of false positives, i.e., non-AF epochs misclassified as AF.

A sensitivity of 96.88%, specificity of 99.26%, PPV of 98.87% and an F-Score of 97.87% was obtained on the AFDB database. Similarly, a sensitivity of 99.26%, a specificity of 97.10%, PPV of 77.91% and an F-Score of 87.30% was obtained on the MITDB database. The relatively lower F-scores on the MITDB database compared to the AFDB database can be attributed to the high imbalance in the proportion of non-AF and AF annotations (nearly 10:1).

TABLE XII

| Fold | Training set F-Score | Validation set F-score |
|---|---|---|
| Fold 1 | 98.68% ± 0.51% | 98.17% ± 0.23% |
| Fold 2 | 98.69% ± 0.53% | 98.10% ± 0.18% |
| Fold 3 | 98.79% ± 0.48% | 97.39% ± 0.26% |
| Fold 4 | 98.70% ± 0.52% | 98.06% ± 0.21% |
| Fold 5 | 98.68% ± 0.51% | 98.26% ± 0.25% |

TABLE XIII

| Dataset | Se | Sp | PPV | FSc |
|---|---|---|---|---|
| AFDB (Training dataset) | 96.88% | 99.26% | 98.87% | 99.27% |
| MITDB (Test Dataset) | 99.26% | 97.10% | 77.91% | 87.30% |

The performance of the above-described AF detection algorithm is compared with other state-of-the-art methods whose results have been reported on the AFDB and/or MITDB databases. These statistics are provided in a table provided in FIG. 25. It can be seen that the $AF_{model}$ performs comparably or better than the other algorithms. The first three methods listed after the first method ($AF_{model}$) in FIG. 25 are heart-rate dependent and do not utilize atrial activity information. In fact, the work presented in (Moody, 1983) is one of the earliest publications in the field of automated AF analysis. Their algorithm considers a three-state (short, regular and long) Markov model for analyzing the RR-interval sequence and the transition probabilities are compared with that of reference AF transition probabilities for rhythm identification. The authors explain that the use of a Markov model in isolation results in unacceptably high false positive rates and hence they include a filtering and interpolation stage along with an ectopic beat removal step to improve their accuracy. Although reducing data storage, the definition of only three states for RR-intervals could sometimes lead to missing crucial heart rate variation information which can consequently render it difficult to distinguish AF from other similar rhythms.

Referring back to FIG. 2, upon completion of the AF detection stage/step 210, an exemplary arrhythmia analysis process 200 can commence with detection of supraventricular ectopic beats 212 and associated arrhythmias 213-216. As mentioned previously, Supraventricular Ectopic Beats (SVEBs) include both PACs and PJCs.

In various embodiments, an exemplary arrhythmia analysis algorithm and related processes in detecting the presence of SVEB is performed on a beat-by-beat basis and is implemented through logical analysis techniques as follows: Step 1: Pre-process an incoming ECG signal; Step 2: Perform ventricular fibrillation/sustained ventricular tachycardia (VF/VT) detection; Step 3: Identify ECG segments with VF/VT and omit them for further analysis; Step 4: Perform R-peak (beat) detection and store the R-peak locations in a vector r peaks. Mark each R-peak as unvisited; and Step 5: Compute an RR-interval between the first two R-peaks using Equation (29) and store this value in the vector rr_series. Mark these two R-peaks as non-SVEB indicating these R-peaks are not supraventricular beats.

For Step 6, If no unvisited R-peaks remain in r_peaks, then the process proceeds to Step 7. Else, the next unvisited R-peak r_i in r_peaks is selected and the following steps are implemented:
(i) Check if r_i is a PVC beat. If so, mark it as non-SVEB and go back to Step 6. Else, continue.
(ii) Check if r_i is part of an AF segment. If so, mark it as non-SVEB and go back to Step 6. Else, continue.
(iii) Compute RR-interval rr_i using Equation (29).
(iv) Check to see if this RR-interval is less than a pre-defined threshold thr_sveb. This threshold is defined as:

$$thr\_sveb = thr * rr\_med \qquad (39)$$

where rr_med is the median of the ten most recent values in the vector rr_series. If rr_series vector contains less than ten values, then take the median of all the values in the vector to compute rr_med. thr is a scaling factor set to 0.875 by default. Note that changing this value will accordingly change the balance between false positives and false negatives.
(v) If the value of rr_i is less than thr_sveb, then mark r_i as SVEB, i.e., indicating that this R-peak is a supraventricular beat and go to Step 6. Else, mark r_i as non-SVEB and append the value rr_i to rr_series.

Figure 26:
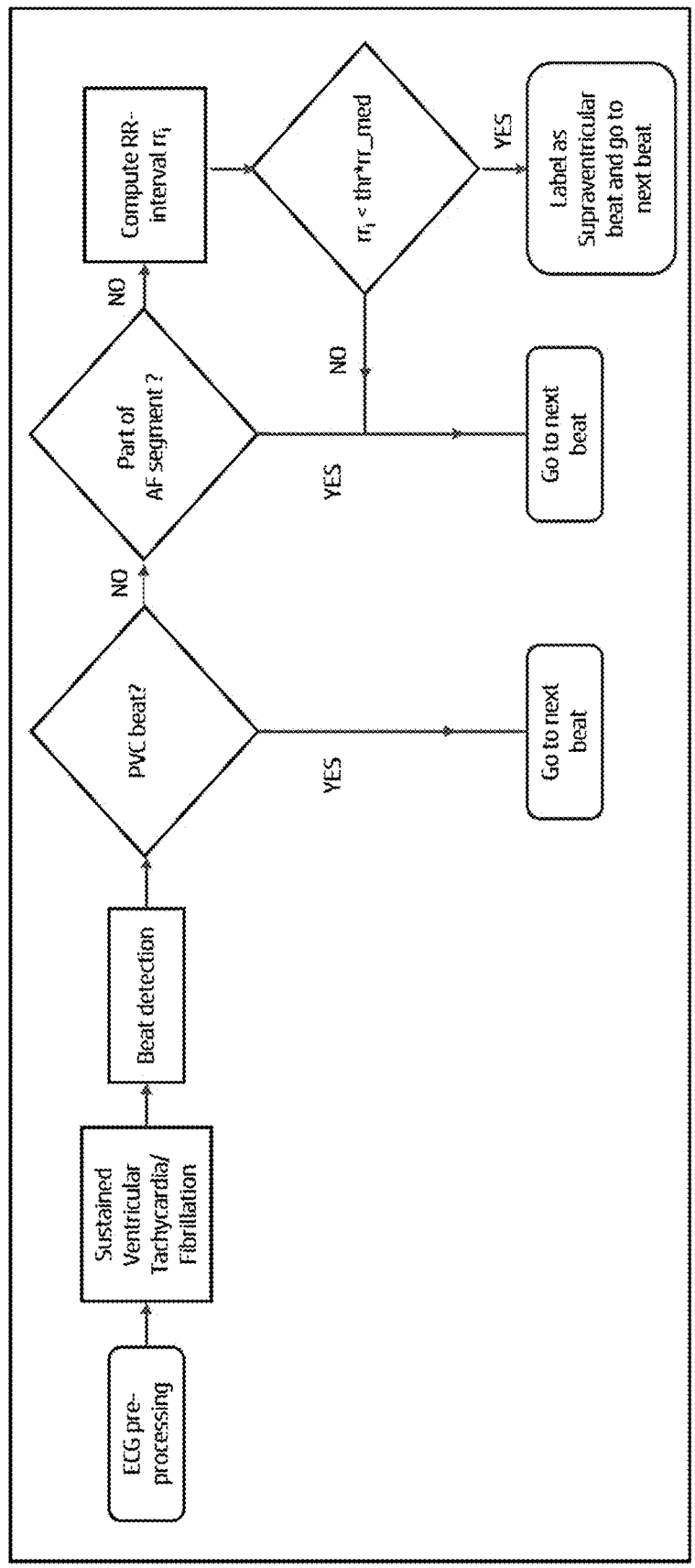
FIG. 26 shows a flow diagram depicting the steps involved in an arrhythmia analysis algorithm and related processes in detecting the presence of Supraventricular Ectopic Beats (SVEBs) in accordance with various embodiments of the present disclosure.

Next, for Step 7, the process returns the r peak vector with R-peak locations along with SVEB/non-SVEB labels for each R-peak. An overview of the above-recited steps are provided in a flow diagram of FIG. 26 and Table XIV presents the tabulated results of the same.

TABLE XIV

| Dataset | Se | PPV | FSc |
|---|---|---|---|
| MITDB | 92.11% | 83.77% | 87.74% |

The occurrence of SVEBs in certain specific patterns gives rise to different supraventricular arrhythmias. Since these patterns are clearly defined in medical literature, simple logical analysis that searches for these patterns is implemented to detect the presence of these arrhythmias. It must be remembered that this logical analysis step is based on beat label information obtained in the SVEB classification stage and hence the detection accuracy for these arrhythmias inherently depends on the accuracy of SVEB detection. These arrhythmias and the logic required to detect them are briefly discussed below.

Supraventricular Bigeminy (SVBI) refers to the occurrence of alternating SVEB and non-SVEB beats. To confirm supraventricular bigeminy, presence of at least three consecutive pairs of Non-SVEB/SVEB beats is required. If SVEB beats are denoted as S and non-SVEB beats are denoted as N, then an exemplary supraventricular arrhythmia analysis algorithm and related processes search for the pattern [NSNSNS . . . ]. Hence at least six beats are required to detect presence of SVBI episodes. The occurrence of two consecutive N beats marks the end of a supraventricular bigeminy episode. To detect another episode, the exemplary algorithm once again searches for the sequence [NSNSNS . . . ] in the remaining beats. Once the sequence is found, it marks the onset of another SVBI episode and continues scanning until it encounters two consecutive N beats which marks the offset of this new episode. This process is repeated for all the remaining beats in the input ECG signal.

Supraventricular Trigeminy (STRI) refers to the occurrence of a SVEB beat after every two consecutive non- SVEB beats. To confirm supraventricular trigeminy, presence of at least three consecutive triplets of the form [NNS] is required. To detect a supraventricular Trigeminy episode, an exemplary supraventricular arrhythmia analysis algorithm and related processes search for the pattern [NNSNNSNNS . . . ]. Hence at least nine beats are required for detection of SVTRI episodes. The occurrence of any beat-triplet other than [NNS] beat-triplet marks the end of a supraventricular trigeminy episode. To detect another episode, the exemplary algorithm once again searches for the sequence [NNSNNSNNS . . . ] in the remaining beats. Once the sequence is found, it marks the onset of another SVTRI episode and continues scanning until it encounters a beat-triplet other than [NNS] which marks the offset of this new episode. This process is repeated for all the remaining beats in the input ECG signal.

Supraventricular Quadrigeminy (SVQUAD) refers to the occurrence of a SVEB beat after every three consecutive non-SVEB beats. To confirm supraventricular quadrigeminy, presence of at least three consecutive quadruplets of the form [NNNs] is required. To detect a supraventricular trigeminy episode, an exemplary supraventricular arrhythmia analysis algorithm and related processes search for the pattern [NNNSNNNSNNNS . . . ]. Hence at least twelve beats are required for detection of SVQUAD episodes. The occurrence of any beat-quadruplet other than [NNNS] beat-triplet marks the end of a supraventricular quadrigeminy episode. To detect another episode, the exemplary algorithm once again searches for the sequence [NNNSNNNSNNNS . . . ] in the remaining beats. Once the sequence is found, it marks the onset of another SVQUAD episode and continues scanning until it encounters a beat-quadruplet other than [NNNS] which marks the offset of this new episode. This process is repeated for all the remaining beats in the input ECG signal.

Supraventricular runs refer to occurrence of three or more consecutive SVEBs at heart rates greater than 100 bpm. At heart rates greater than 120 bpm, these rhythms are also known as Supraventricular Tachycardia episodes. This includes sinus tachycardia, atrial tachycardia and junctional tachycardia. To detect supraventricular runs, an exemplary supraventricular arrhythmia analysis algorithm and related processes search groups of three or more consecutive SVEB beats. For every group of three or more consecutive SVEB beats, the mean heart rate is computed as follows:

$$RR_{group} = \frac{1}{n-1}\sum_{k=1}^{n-1} rr_k \quad (40)$$

$$HR_{group} = \frac{Fs * 60}{RR_{group}} \quad (41)$$

where n is the number of SVEBs in the beat group, $rr_k$ is the kth RR-interval in the group, computed using Equation (29), and Fs is the sampling frequency. If the value of $HR_{group}$ exceeds 100 bpm, that group of beats is labeled as a supraventricular run episode.

Supraventricular couplets or pairs refer to occurrence of exactly two consecutive SVEBs at heart rates greater than 100 bpm. To detect supraventricular couplets, an exemplary supraventricular arrhythmia analysis algorithm and related processes search for the presence of [SS] pattern in the beats and each such pair is marked as a supraventricular couplet episode.

Sinus bradycardia (SBR) refers to the condition where the SA node fires slower than normal for a patient's age. Heart rates lower than 50 bpm usually fall under the category of SBR. When the heart rates goes below 40 bpm, it is termed Extreme Bradycardia or Severe Sinus Bradycardia. To detect SBR, an exemplary supraventricular arrhythmia analysis algorithm and related processes search for groups of five or more consecutive beats whose mean heart rate (computed using Equation (41)) is less than 50 bpm. For every such group found, the exemplary algorithm does the following: (i) Check if the beats in the group include VF/VT segments or PVC beats or AF beats; and (ii) If none of the above conditions are met, then label that group of five or more consecutive beats as a Sinus bradycardia episode.

In general, the work presented in the present disclosure is translational in nature and can be used in real-world settings. As discussed in connection with FIG. 3A, this is demonstrated by deploying the disclosed methods and algorithms in a fully functional cloud platform, referred to as AutoECG. AutoECG is a first-of-its-kind web service that facilitates automated cardiac arrhythmia detection using information extracted from single-lead electrocardiogram (ECG) signals. As previously discussed, the arrhythmias analysis techniques disclosed in the present disclosure, and therefore capable of being deployed in AutoECG, are capable of detecting a multitude of cardiac arrhythmias (e.g., 15 different cardia arrhythmias). Given that more than four million Americans are affected by some form of arrhythmia and that delayed diagnosis can increase severity of these arrhythmias, it imperative to utilize a system such as AutoECG that aids in continuous ECG monitoring to help provide timely care and treatment in out-of-hospital settings. More importantly, the software deployed in AutoECG includes algorithms that are capable of accurately detecting ventricular arrhythmias such as PVC, VF, VT and other ventricular rhythms.

In an exemplary embodiment, the codebase deployed in AutoECG, pertaining to arrhythmia detection algorithms, is written in Python 3.6, and the AutoECG platform features a 64-bit dual-core Intel® Xeon® Platinum 8175M CPU processor operating at a clock frequency of 2.50 GHz. In various embodiments, the hardware platform is provided by Amazon Web Services in the form of Infrastructure as a Service (IaaS). The algorithms deployed in AutoECG are device-agnostic and are well-equipped to analyze data from a diverse range of ECG acquisition devices. Additionally, the AutoECG system is designed to handle ECG signals spanning 30 seconds to 24 hours, thus facilitating real-time analysis (wearables) as well as overnight monitoring (hospitals, bedside monitoring, etc.). Implementing a fully automated arrhythmia system, such as AutoECG, minimizes burden on physicians and helps them prioritize their patients thus allowing them to attend to more patients as well as speeding up diagnosis and treatment. Such systems also have the advantage that they can be easily integrated into telemedicine platforms for remote delivery of healthcare services.

Figure 27:
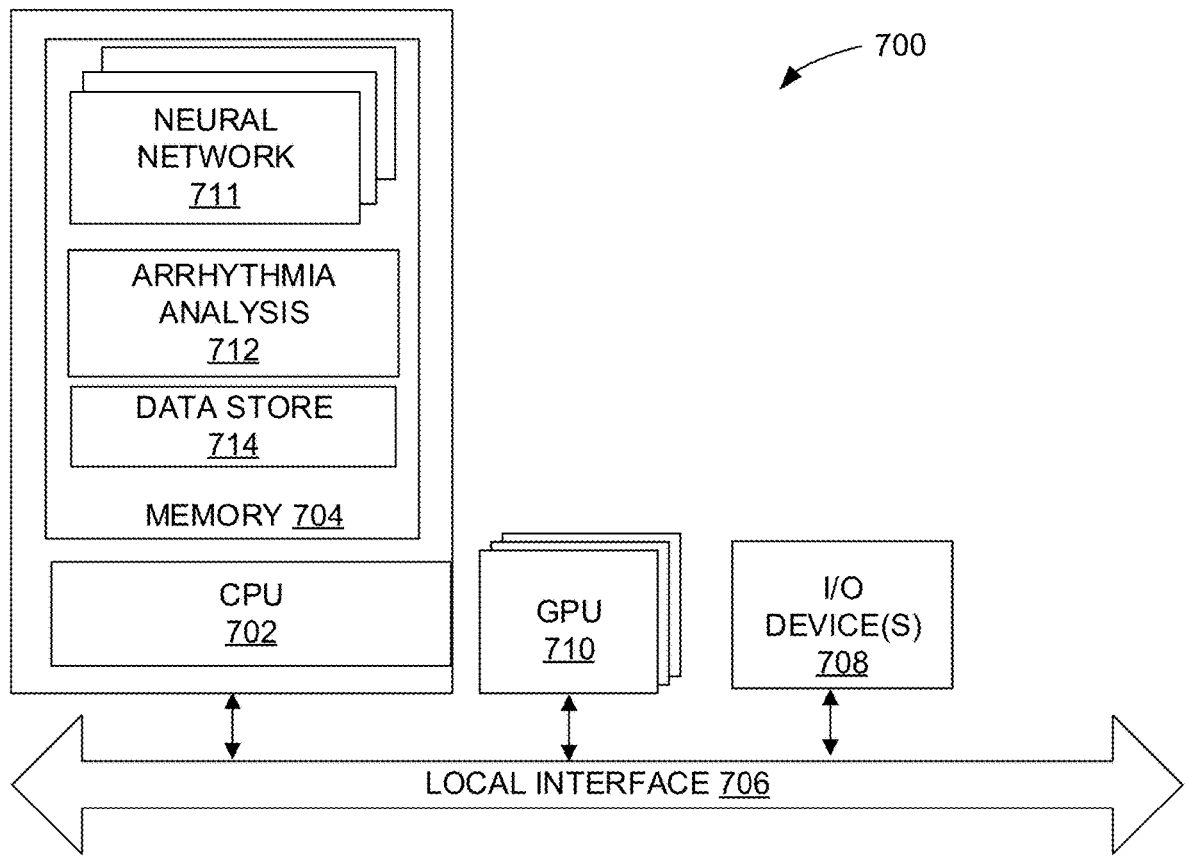
FIG. 27 provides a schematic of a computing device according to an exemplary embodiment of the present disclosure.

FIG. 27 provides a schematic of a computing device 700 according to one embodiment of the present disclosure. In example embodiments, the computing device 700 may be configured to perform various machine learning techniques, such as random forest, convolutional autoencoders, and the like, as provided in the present disclosure, and/or train a deep neural network. In some examples, the computing device 700 may comprise or otherwise be in communication with an ECG machine, user devices, etc. In various embodiments, the computing device 700 may be part of a cloud-based computing platform that provides hosted services to end users. An exemplary computing device 700 includes at least one processor circuit, for example, having a processor (CPU) 702 and a memory 704, both of which are coupled to a local interface 706, and one or more input and output (I/O) devices 708. The local interface 706 may comprise, for example, a data bus with an accompanying address/control bus or other bus structure as can be appreciated. The computing device 700 further includes Graphical Processing Unit(s) (GPU) 710 that are coupled to the local interface 706 and may utilize memory 704 and/or may have its own dedicated memory. The CPU and/or GPU(s) can perform various operations such as image enhancement, graphics rendering, image/video processing, recognition (e.g., object recognition, feature recognition, etc.), image stabilization, machine learning, filtering, image classification, and any of the various operations described herein.

Stored in the memory 704 are both data and several components that are executable by the processor 702. In particular, stored in the memory 704 and executable by the processor 702 are code for implementing one or more neural networks 711 (or other machine learning models) and arrhythmia analysis logic/instructions 712 in accordance with embodiments of the present disclosure. Also stored in the memory 704 may be a data store 714 and other data. The data store 714 can include a database of stored data files (e.g., stored ECG waveform data files), and potentially other data. In addition, an operating system may be stored in the memory 704 and executable by the processor 702. The I/O devices 708 may include input devices, for example but not limited to, a keyboard, mouse, an ECG machine, etc. Furthermore, the I/O devices 708 may also include output devices, for example but not limited to, a printer, display, etc.

Certain embodiments of the present disclosure can be implemented in hardware, software, firmware, or a combination thereof. If implemented in software, exemplary arrhythmia analysis logic or functionality are implemented in software or firmware that is stored in a memory and that is executed by a suitable instruction execution system. If implemented in hardware, the arrhythmia analysis logic or functionality can be implemented with any or a combination of the following technologies, which are all well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

It should be emphasized that the above-described embodiments are merely possible examples of implementations, merely set forth for a clear understanding of the principles of the present disclosure. Many variations and modifications may be made to the above-described embodiment(s) without departing substantially from the principles of the present disclosure. For example, information from multi-lead signals can be used to create a rich set of features that can provide enhanced arrhythmia detection performance. Additional algorithms for detection of a more diverse range of arrhythmias are also contemplated. All such modifications and variations are intended to be included herein within the scope of this disclosure.

Therefore, at least the following is claimed:

1. An arrhythmia analysis method comprising:

training, by an at least one computing device, a noise suppression model with training data comprising electrocardiogram (ECG) waveform signals;

generating, by the at least one computing device, model weights for the noise suppression model during the training of the noise suppression model;

initializing, by the at least one computing device, the noise suppression model with the model weights for the noise suppression model generated during the training of the noise suppression model;

training, by the at least one computing device, a noise detection model with training data comprising noisy ECG waveform signals;

generating, by the at least once computing device, model weights for the noise detection model during the training of the noise detection model;

initializing, by the at least one computing device, the noise detection model with the model weights for the noise detection model generated during the training of the noise detection model;

training, by the at least one computing device, a beat extraction model with training data comprising denoised ECG waveform signals;

generating, by the at least once computing device, model parameters for the beat extraction model during the training of the beat extraction model;

initializing, by the at least one computing device, the beat extraction model with the model parameters generated during the training of the beat extraction model;

acquiring, by the at least one computing device, an electrocardiogram (ECG) waveform signal of a subject at a set sampling frequency rate;

applying, by the at least one computing device, the acquired ECG waveform signal as input to the noise suppression model and processing, by the at least one computing device using the noise suppression model, the acquired ECG waveform signal to remove low-frequency noise and high-frequency noise artifacts and form a denoised ECG waveform signal;

applying, by the at least one computing device, the denoised ECG waveform signal as input to the noise detection model and processing, by the at least one computing device using the noise detection model, the denoised ECG waveform signal to remove low-quality segments and form a high-quality ECG waveform signal;

analyzing, by the at least one computing device, the high-quality ECG waveform signal to detect a presence of a beat-independent ventricular arrhythmia within the high-quality ECG waveform signal;

processing, by the at least one computing device using the beat extraction model, the denoised ECG waveform signal to extract beat (R-peak) locations corresponding to QRS complexes from the denoised ECG waveform signal;

analyzing, by the at least one computing device using the beat extraction model, the denoised ECG waveform signal to detect a presence of a beat-dependent ventricular arrhythmia within the denoised ECG waveform signal based on the extracted beat (R-peak) locations of the denoised ECG waveform signal;

analyzing, by the at least one computing device using the beat extraction model, the denoised ECG waveform signal to detect a presence of one or more supraventricular arrhythmias within the denoised ECG waveform signal based on the extracted beat (R-peak) locations of the denoised ECG waveform signal, wherein the analysis of the denoised ECG waveform signal to detect the presence of one or more supraventricular arrhythmias comprises performing supraventricular ectopic beats (SVEBs) classifications of the denoised ECG waveform signal using semi-supervised autoencoder and random forest machine learning techniques; and outputting, by the at least one computing device, a report containing one or more arrhythmias detected by the analyzing steps.

2. The method of claim 1, wherein the low-frequency noise artifact is removed by application of stationary wavelet transforms to the acquired ECG waveform signal.

3. The method of claim 1, wherein the high-frequency noise artifact is removed by application of Convolutional Autoencoder techniques.

4. The method of claim 1, wherein the low-quality segments are corrupted by electrode motion artifacts and are removed by application of a convolutional neural network-based binary classifier.

5. The method of claim 1, wherein beat-independent ventricular arrhythmia is analyzed using random forest classifier machine learning techniques.

6. The method of claim 1, wherein a convolutional autoencoder is trained to identify potential QRS complexes and an adaptive thresholding is applied to the potential QRS complexes to accurately identify the beat (R-peak) locations corresponding to the QRS complexes present in the denoised ECG waveform signal.

7. The method of claim 1, wherein the denoised ECG waveform signal is processed to perform premature ventricular complexes (PVC) classifications of the denoised ECG signal using semi-supervised autoencoder and random forest machine learning techniques.

8. The method of claim 7, wherein the presence of one or more beat-dependent ventricular arrhythmias is detected using logical analysis of patterns of the PVC classifications of the denoised ECG waveform signal.

9. The method of claim 1, wherein a presence of an atrial fibrillation supraventricular arrhythmia is detected using machine learning employing 8-state Markov models and random forest classifier techniques.

10. The method of claim 1, wherein the presence of one or more supraventricular arrhythmia is detected using logical analysis of patterns of SVEB beats within the denoised ECG waveform signal.

11. The method of claim 1, wherein the at least one computing device is configured to detect one or more beat-independent ventricular arrhythmias including sustained ventricular tachycardia, ventricular fibrillation, and ventricular flutter.

12. The method of claim 1, wherein the at least one computing device is configured to detect one or more beat-dependent ventricular arrhythmias including ventricular bigeminy, ventricular trigeminy, ventricular quadrigeminy, ventricular runs and ventricular couplets.

13. The method of claim 1, wherein the at least one computing device is configured to detect one or more supraventricular arrhythmias including supraventricular bigeminy, supraventricular trigeminy, supraventricular quadrigeminy, supraventricular runs, supraventricular couplets, and sinus bradycardia.

14. The method of claim 1, further comprising:
receiving, by the at least one computing device, electrocardiogram data representing an electrocardiogram waveform signal of the subject at first sampling frequency rate; and
resampling, by the at least one computing device, the electrocardiogram waveform signal at the first sampling frequency rate to the set sampling frequency rate to form the acquired electrocardiogram waveform signal.

15. An arrhythmia analysis system comprising:
a computing device having a memory and a processor, wherein the processor is configured to:
train a noise suppression model with training data comprising electrocardiogram (ECG) waveform signals;
generate model weights for the noise suppression model during the training of the noise suppression model;
initialize the noise suppression model with the model weights for the noise suppression model generated during the training of the noise suppression model;
train a noise detection model with training data comprising noisy ECG waveform signals;
generate model weights for the noise detection model during the training of the noise detection model;
initialize the noise detection model with the model weights for the noise detection model generated during the training of the noise detection model;
train a beat extraction model with training data comprising denoised ECG waveform signals;
generate model parameters for the beat extraction model during the training of the beat extraction model;
initialize the beat extraction model with the model parameters generated during the training of the beat extraction model;
acquire an electrocardiogram (ECG) waveform signal of a subject at a set sampling frequency rate;
apply the acquired ECG waveform signal as input to the noise suppression model and process the acquired ECG waveform signal to remove low-frequency noise and high-frequency noise artifacts and form a denoised ECG waveform signal;
process the denoised ECG waveform signal to remove low-quality segments corrupted by electrode motion artifacts and form a high-quality ECG waveform signal;
apply the denoised ECG waveform signal as input to the noise detection model and analyze the high-quality ECG waveform signal to detect a presence of a beat-independent ventricular arrhythmia within the high-quality ECG signal;
process, using the beat extraction model, the denoised ECG waveform signal to extract beat (R-peak) locations corresponding to QRS complexes from the denoised ECG waveform signal;
analyze, using the beat extraction model, the denoised ECG signal to detect a presence of a beat-dependent ventricular arrhythmia within the denoised ECG waveform signal based on the extracted beat (R-peak) locations of the denoised ECG waveform signal;
analyze, using the beat extraction model, the denoised ECG waveform signal to detect a presence of one or more supraventricular arrhythmias within the denoised ECG waveform signal based on the extracted beat (R-peak) locations of the denoised ECG waveform signal, wherein the analysis of the denoised ECG waveform signal to detect the presence of one or more supraventricular arrhythmias comprises performing supraventricular ectopic beats (SVEBs) classifications of the denoised ECG signal using semi-supervised autoencoder and random forest machine learning techniques; and output a report containing one or more arrhythmias detected by the analyzing steps.

16. The system of claim 15, further comprising an ECG machine that is configured to sense the ECG waveform signal.

17. The system of claim 15, wherein the computing device performs the analyzing steps and delivers the output report as hosted services over the Internet.

18. The system of claim 15, wherein the ECG waveform signal comprises a single-lead ECG waveform signal.

19. The system of claim 15, wherein the computing device is configured to detect one or more beat-independent ventricular arrhythmias including sustained ventricular tachycardia, ventricular fibrillation, and ventricular flutter, wherein the computing device is configured to detect one or more beat-dependent ventricular arrhythmias including ventricular bigeminy, ventricular trigeminy, ventricular quadrigeminy, ventricular runs, and ventricular couplets, and wherein the computing device is configured to detect one or more supraventricular arrhythmias including atrial fibrillation, supraventricular bigeminy, supraventricular trigeminy, supraventricular quadrigeminy, supraventricular runs, supraventricular couplets, and sinus bradycardia.

20. The system of claim 15, further comprising a client computing device that is configured to transmit the electrocardiogram (ECG) waveform signal of the subject to the computing device and is configured to receive the report from the computing device, wherein the client computing devices comprises a smart phone or a smart watch.

21. An arrhythmia analysis method comprising:

training, by an at least one computing device, a noise suppression model with training data comprising electrocardiogram (ECG) waveform signals;

generating, by the at least one computing device, model weights for the noise suppression model during the training of the noise suppression model;

initializing, by the at least one computing device, the noise suppression model with the model weights for the noise suppression model generated during the training of the noise suppression model;

training, by the at least one computing device, a noise detection model with training data comprising noisy ECG waveform signals;

generating, by the at least once computing device, model weights for the noise detection model during the training of the noise detection model;

initializing, by the at least one computing device, the noise detection model with the model weights for the noise detection model generated during the training of the noise detection model;

training, by the at least one computing device, a beat extraction model with training data comprising denoised ECG waveform signals;

generating, by the at least once computing device, model parameters for the beat extraction model during the training of the beat extraction model;

initializing, by the at least one computing device, the beat extraction model with the model parameters generated during the training of the beat extraction model;

acquiring, by the at least one computing device, an electrocardiogram (ECG) waveform signal of a subject at a set sampling frequency rate;

applying, by the at least one computing device, the acquired ECG waveform signal as input to the noise suppression model and processing, by the at least one computing device using the noise suppression model, the acquired ECG waveform signal to remove low-frequency noise and high-frequency noise artifacts and form a denoised ECG waveform signal;

applying, by the at least one computing device, the denoised ECG waveform signal as input to the noise detection model and processing, by the at least one computing device using the noise detection model, the denoised ECG waveform signal to remove low-quality segments and form a high-quality ECG waveform signal;

analyzing, by the at least one computing device, the high-quality ECG waveform signal to detect a presence of a beat-independent ventricular arrhythmia within the high-quality ECG waveform signal;

processing, by the at least one computing device using the beat extraction model, the denoised ECG waveform signal to extract beat (R-peak) locations corresponding to QRS complexes from the denoised ECG waveform signal;

analyzing, by the at least one computing device using the beat extraction model, the denoised ECG waveform signal to detect a presence of a beat-dependent ventricular arrhythmia within the denoised ECG waveform signal based on the extracted beat (R-peak) locations of the denoised ECG waveform signal;

analyzing, by the at least one computing device using the beat extraction model, the denoised ECG waveform signal to detect a presence of one or more supraventricular arrhythmias within the denoised ECG waveform signal based on the extracted beat (R-peak) locations of the ECG waveform signal, wherein a presence of an atrial fibrillation supraventricular arrhythmia is detected using machine learning employing 8-state Markov models and random forest classifier techniques; and outputting, by the at least one computing device, a report containing one or more arrhythmias detected by the analyzing steps.

* * * * *